US012582403B2

(12) United States Patent
Mayer et al.

(10) Patent No.: US 12,582,403 B2
(45) **Date of Patent: \*Mar. 24, 2026**

(54) DEVICES FOR TREATING VASCULAR MALFORMATIONS

(71) Applicant: ENDOSTREAM MEDICAL LTD., Or Akiva (IL)

(72) Inventors: Danel Mayer, Tel Aviv (IL); Alon May, Caesarea (IL); Yuval Shezifi, Haifa (IL)

(73) Assignee: ENDOSTREAM MEDICAL LTD., Or Akiva (IL)

( * ) Notice: Subject to any disclaimer, the term of this patent is extended or adjusted under 35 U.S.C. 154(b) by 51 days.

This patent is subject to a terminal disclaimer.

(21) Appl. No.: 18/782,707

(22) Filed: Jul. 24, 2024

(65) Prior Publication Data

US 2024/0374260 A1 Nov. 14, 2024

Related U.S. Application Data

(63) Continuation of application No. 17/418,026, filed as application No. PCT/IL2019/051401 on Dec. 24, 2019, now Pat. No. 12,059,156.

(Continued)

(51) Int. Cl.
*A61B 17/12* (2006.01)
*A61B 17/00* (2006.01)

(52) U.S. Cl.
CPC .. *A61B 17/12113* (2013.01); *A61B 17/12145* (2013.01); *A61B 2017/00867* (2013.01)

(58) Field of Classification Search
CPC ........ A61B 17/12113; A61B 17/12145; A61B 17/1214; A61B 17/1215; A61B 17/12031; A61B 2017/00867; A61B 2017/12054

(Continued)

(56) References Cited

U.S. PATENT DOCUMENTS

| | | | |
|---|---|---|---|
| 5,350,397 A | 9/1994 | Palermo et al. |
| 5,649,949 A | 7/1997 | Wallace et al. |
| (Continued) | | | |

FOREIGN PATENT DOCUMENTS

| | | |
|---|---|---|
| CN | 202136073 U | 2/2012 |
| CN | 203787320 U | 8/2014 |
| (Continued) | | |

OTHER PUBLICATIONS

An English Translation of an Office Action dated Jun. 2, 2020, which issued during the prosecution of Chinese Patent Application No. 201780051968.9.

(Continued)

*Primary Examiner* — Tan-Uyen T Ho
*Assistant Examiner* — Osama Nemer
(74) *Attorney, Agent, or Firm* — Sughrue Mion, PLLC

(57) ABSTRACT

An apparatus is provided for treating a vascular malformation. The apparatus includes an orifice section, an intra-vascular-malformation docking section, and a connecting section. The apparatus is configured such that, when unconstrained the orifice section is shaped so as to define an orifice-section curve that winds at least 2.5 turns around an orifice-section central axis at a changing distance from the orifice-section central axis, the intra-vascular-malformation docking section is shaped so as to define a docking-section curve that winds between 0.5 and 2 turns around a docking-section central axis at a changing or constant distance from the docking-section central axis, and a slope of the connecting-section is greater than a slope of the orifice-section. Other embodiments are also described.

22 Claims, 10 Drawing Sheets

Related U.S. Application Data

(60) Provisional application No. 62/785,013, filed on Dec. 26, 2018.

(58) Field of Classification Search
USPC ........................................................ 606/200
See application file for complete search history.

(56) References Cited

U.S. PATENT DOCUMENTS

| | | | |
|---|---|---|---|
| 5,749,891 | A | 5/1998 | Ken et al. |
| 5,935,148 | A | 8/1999 | Villar et al. |
| 6,036,720 | A | 3/2000 | Abrams et al. |
| 6,306,141 | B1 | 10/2001 | Jervis |
| 6,338,736 | B1 | 1/2002 | Boosfeld et al. |
| 6,371,972 | B1 | 4/2002 | Wallace et al. |
| 6,383,174 | B1 | 5/2002 | Eder |
| 6,428,557 | B1 * | 8/2002 | Hilaire ............. A61B 17/12022 |
| | | | 606/200 |
| 6,506,204 | B2 | 1/2003 | Mazzocchi |
| 6,551,305 | B2 | 4/2003 | Ferrera et al. |
| 6,589,265 | B1 | 7/2003 | Palmer et al. |
| 6,740,096 | B2 | 5/2004 | Teague et al. |
| 6,790,218 | B2 | 9/2004 | Jayaraman |
| 7,128,736 | B1 | 10/2006 | Abrams et al. |
| 7,229,461 | B2 | 6/2007 | Chin et al. |
| 7,323,000 | B2 | 1/2008 | Monstdt et al. |
| 7,377,932 | B2 | 5/2008 | Mitelberg et al. |
| 7,569,066 | B2 | 8/2009 | Gerberding et al. |
| 8,007,509 | B2 | 8/2011 | Buiser et al. |
| 8,333,796 | B2 | 12/2012 | Tompkins et al. |
| 8,444,667 | B2 | 5/2013 | Porter |
| 8,518,064 | B2 | 8/2013 | Kurrus et al. |
| 8,570,343 | B2 | 10/2013 | Halstead |
| 8,747,454 | B2 | 6/2014 | Khairkhahan et al. |
| 8,753,362 | B2 * | 6/2014 | Widomski ......... A61B 17/0057 |
| | | | 606/151 |
| 8,764,772 | B2 | 7/2014 | Tekulve |
| 8,906,057 | B2 | 12/2014 | Connor et al. |
| 9,138,232 | B2 | 9/2015 | Connor |
| 9,629,635 | B2 | 4/2017 | Hewitt et al. |
| 10,016,272 | B2 * | 7/2018 | Spence ................. A61F 2/2463 |
| 10,413,285 | B2 * | 9/2019 | Kerr ................. A61B 17/12109 |
| 10,869,673 | B2 * | 12/2020 | Zhang ............. A61B 17/12145 |
| 11,103,253 | B2 | 8/2021 | Mai |
| 11,484,322 | B2 * | 11/2022 | Connor ............. A61B 17/1214 |
| 2002/0049468 | A1 | 4/2002 | Streeter et al. |
| 2002/0107534 | A1 | 8/2002 | Schaefer et al. |
| 2002/0169473 | A1 | 11/2002 | Sepetka et al. |
| 2003/0055451 | A1 | 3/2003 | Jones et al. |
| 2003/0216772 | A1 | 11/2003 | Konya et al. |
| 2004/0034386 | A1 | 2/2004 | Fulton et al. |
| 2004/0098027 | A1 | 5/2004 | Teoh et al. |
| 2004/0167597 | A1 | 8/2004 | Costantino et al. |
| 2005/0038460 | A1 | 2/2005 | Jayaraman |
| 2005/0107823 | A1 | 5/2005 | Leone et al. |
| 2005/0187564 | A1 | 8/2005 | Jayaraman |
| 2005/0251154 | A1 * | 11/2005 | Chanduszko ...... A61B 17/0057 |
| | | | 606/151 |
| 2006/0052821 | A1 * | 3/2006 | Abbott ................. A61B 17/064 |
| | | | 606/213 |
| 2006/0155323 | A1 | 7/2006 | Porter et al. |
| 2006/0206199 | A1 | 9/2006 | Churchwell et al. |
| 2007/0083230 | A1 | 4/2007 | Javois |
| 2007/0123928 | A1 | 5/2007 | Farnan |
| 2007/0150045 | A1 | 6/2007 | Ferrera |
| 2008/0114436 | A1 | 5/2008 | Dieck et al. |
| 2008/0300616 | A1 | 12/2008 | Que et al. |
| 2009/0099647 | A1 | 4/2009 | Glimsdale et al. |
| 2009/0216265 | A1 | 8/2009 | DeVries et al. |
| 2010/0121350 | A1 | 5/2010 | Mirigian |
| 2011/0022149 | A1 | 1/2011 | Cox et al. |
| 2012/0071911 | A1 | 3/2012 | Sadasivan et al. |

| | | | |
|---|---|---|---|
| 2012/0143237 | A1 | 6/2012 | Cam et al. |
| 2013/0296917 | A1 * | 11/2013 | Rees ................ A61B 17/12154 |
| | | | 606/200 |
| 2014/0180377 | A1 | 6/2014 | Bose et al. |
| 2014/0277095 | A1 * | 9/2014 | Kerr ................. A61B 17/12109 |
| | | | 606/200 |
| 2016/0022445 | A1 * | 1/2016 | Ruvalcaba ....... A61B 17/12163 |
| | | | 606/198 |
| 2016/0120551 | A1 * | 5/2016 | Connor ..................... A61F 2/91 |
| | | | 606/200 |
| 2017/0086851 | A1 * | 3/2017 | Wallace ............. A61B 17/1215 |
| 2017/0135701 | A1 | 5/2017 | Beckham et al. |
| 2017/0150971 | A1 | 6/2017 | Hines |
| 2017/0333678 | A1 | 11/2017 | Bowman et al. |
| 2017/0367708 | A1 * | 12/2017 | Mayer .............. A61B 17/12036 |
| 2018/0049859 | A1 * | 2/2018 | Stoppenhagen . A61B 17/12172 |
| 2018/0092690 | A1 * | 4/2018 | Nair ......................... G06T 19/20 |
| 2018/0263630 | A1 * | 9/2018 | Tsukumo ......... A61B 17/12031 |
| 2019/0209181 | A1 * | 7/2019 | Mayer .............. A61B 17/12113 |

FOREIGN PATENT DOCUMENTS

| | | |
|---|---|---|
| EP | 0765636 A2 | 4/1997 |
| WO | 95/25480 A1 | 9/1995 |
| WO | 2012/158883 A1 | 11/2012 |
| WO | 2014/165256 A2 | 10/2014 |
| WO | 2016/108241 A1 | 7/2016 |
| WO | 2017/221252 A1 | 12/2017 |
| WO | 2020/148768 A1 | 7/2020 |

OTHER PUBLICATIONS

An EP Communication in Appl. No. 17814898.7, dated Oct. 5, 2020.

An Invitation to pay additional fees dated Mar. 30, 2020, which issued during the prosecution of Applicant's PCT/IL2019/051401.

An ISR and Written Opinion issued in PCT/IL2019/051401, dated Jun. 24, 2020.

Communication dated Oct. 21, 2019 from the United State Patent and Trademark Office in U.S. Appl. No. 15/540,664.

Communication issued Feb. 3, 2020 by the European Patent Office in application No. 17814898.7.

Nit-Occlud PDA, pfm medical (Jun. 2012).

Medtronic EV3 Axium Youtube excerpts downloaded Aug. 13, 2018.

An International Search Report and a Written Opinion both dated Oct. 3, 2017, which issued during the prosecution of Applicant's PCT/IL2017/050694.

An International Search Report and a Written Opinion both dated Apr. 19, 2016, which issued during the prosecution of Applicant's PCT/IL2015/051271.

U.S. Appl. No. 62/352,578, filed Jun. 21, 2016.

U.S. Appl. No. 62/444,963, filed Jan. 11, 2017.

Office Action dated Sep. 2, 2020, issued by the United States Patent and Trademark Office in counterpart U.S. Appl. No. 16/311,744.

Notice of Allowance dated Dec. 14, 2020, issued by the United States Patent and Trademark Office in counterpart U.S. Appl. No. 16/311,744.

A Non-Final Office Action issued in U.S. Appl. No. 17/216,836, dated Nov. 10, 2022.

A Non-Final Office Action, dated Jan. 19, 2023, issued in U.S. Appl. No. 16/778,581.

United States Office Action dated Jun. 5, 2023 in U.S. Appl. No. 17/418,026.

United States Office Action dated Dec. 19, 2023 in U.S. Appl. No. 17/418,026.

United States Advisory Action dated Mar. 1, 2024 in U.S. Appl. No. 17/418,026.

United States Notice of Allowance dated Apr. 17, 2024 in U.S. Appl. No. 17/418,026.

* cited by examiner

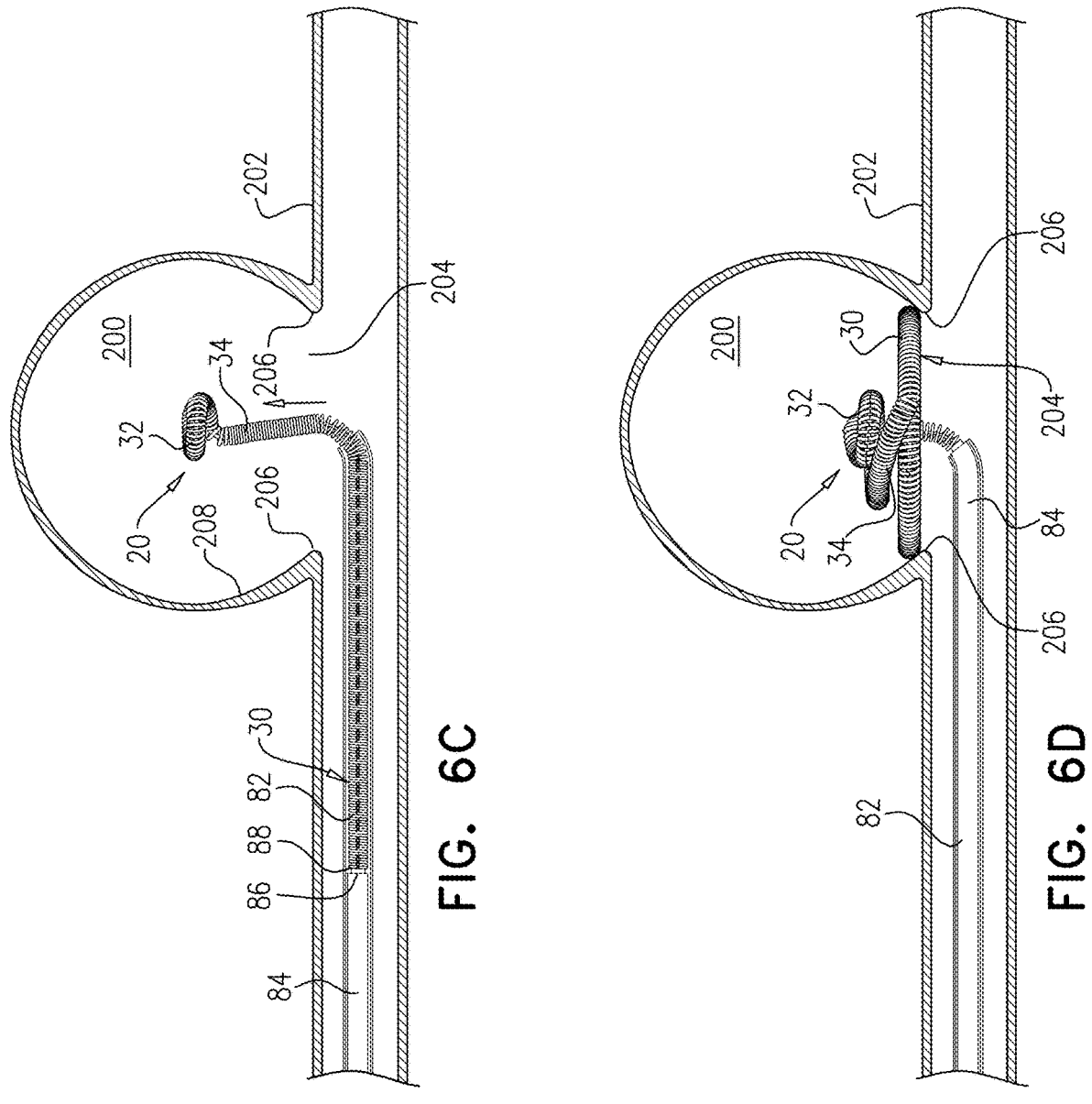

DEVICES FOR TREATING VASCULAR MALFORMATIONS

CROSS-REFERENCE TO RELATED APPLICATIONS

The present application is a continuation of U.S. application Ser. No. 17/418,026, filed Jun. 24, 2021, now U.S. Pat. No. 12,059,156, which is the US national stage of International Application PCT/IL2019/051401, filed Dec. 24, 2019, which published as PCT Publication WO 2020/136643 to Mayer et al. and claims priority from U.S. Provisional Application 62/785,013, filed Dec. 26, 2018. All of the above-referenced applications are assigned to the assignee of the present application and incorporated herein by reference.

FIELD OF THE APPLICATION

The present invention relates generally to minimally-invasive techniques for treating vascular malformations such as aneurysms.

BACKGROUND OF THE APPLICATION

An aneurysm is an abnormal local dilation of an artery caused by a weakening of the artery wall. In the past, cerebral aneurysms were frequently treated by direct surgical intervention, such as by installing a clip around the base of the aneurysm to prevent passage of blood between the aneurysm and the lumen of the vessel. Attempts have then been made to develop minimally-invasive techniques for treating such aneurysms, for example, by filling the aneurysm with endovascular embolization coils, such that the aneurysm eventually becomes a solid mass of coils and thrombus.

SUMMARY OF THE APPLICATION

In some embodiments of the present invention, apparatus is provided for treating a vascular malformation. The apparatus is configured to bridge the neck of a vascular malformation, such as an aneurysm, e.g., a wide-necked aneurysm, in order to prevent coil herniation. The apparatus comprises an orifice section, an intra-vascular-malformation docking section, and a connecting section. The orifice section is configured to bridge the neck of the vascular malformation, which helps prevent coil herniation, i.e., endovascular embolization coils protruding from the aneurysm. The intra-vascular-malformation docking section is configured to facilitate entanglement with endovascular embolization coils, which helps connect the apparatus with the endovascular embolization coils to create a single mass.

The apparatus is typically configured such that, when unconstrained (by the patient's anatomy, a microcatheter, or otherwise):

the orifice section is shaped so as to define an orifice-section curve that winds at least 2 turns (typically at least 2.5 turns) around an orifice-section central axis at a changing distance from the orifice-section central axis, the intra-vascular-malformation docking section is shaped so as to define a docking-section curve that winds between 0.5 and 2 turns (e.g., between 0.75 and 2 turns, such as between 1 and 2 turns) around a docking-section central axis at a changing or constant distance from the docking-section central axis, and the connecting section connects the orifice-section curve with the docking-section curve.

Providing the docking-section curve with only between 0.5 and 2 turns generally facilitates easier deployment of the intra-vascular-malformation docking section in the aneurysm than if the docking-section curve included a greater number of turns, while providing a similar level of entanglement with endovascular embolization coils.

In some embodiments of the present invention, apparatus is provided for treating a vascular malformation. The apparatus is configured to bridge the neck of a vascular malformation, such as an aneurysm, e.g., a wide-necked aneurysm. The apparatus comprises an orifice section, an occlusion section, and a connecting section. The orifice section is configured to bridge the neck of the vascular malformation, which blocks blood flow into the aneurysm, thereby embolizing the aneurysm. The occlusion section is configured to at least partially occlude an orifice-section central opening.

The apparatus is typically configured such that, when unconstrained (by the patient's anatomy, a microcatheter, or otherwise):

the orifice section is shaped so as to define an orifice-section curve that winds at least 2.5 turns around an orifice-section central axis at a changing distance from the orifice-section central axis, the occlusion section is shaped so as to define an occlusion-section curve that winds at least 2 turns around an occlusion-section central axis at a changing distance from the occlusion-section central axis, the connecting section connects the orifice-section curve with the occlusion-section curve, the orifice-section curve defines the above-mentioned orifice-section central opening having an orifice-section-central-opening cross-sectional area equal to at least 2% of an overall-orifice-section cross-sectional area of the orifice-section curve defined by an outermost loop of the orifice-section curve, the orifice-section-central-opening cross-sectional area and the overall-orifice-section cross-sectional area measured perpendicular to the orifice-section central axis, the orifice-section central axis and the occlusion-section central axis are not coaxial, and a projection of the occlusion-section curve occludes at least 25% (e.g., at least 50%) of the orifice-section-central-opening cross-sectional area; the projection of the occlusion-section curve is in a direction along the orifice-section central axis, onto an orifice-section plane perpendicular to the orifice-section central axis.

There is therefore provided, in accordance with an application of the present invention, apparatus for treating a vascular malformation, the apparatus including:

an orifice section;

an occlusion section; and a connecting section, wherein the apparatus is configured such that, when the apparatus is unconstrained:

the orifice section is shaped so as to define an orifice-section curve that winds at least 2.5 turns around an orifice-section central axis at a changing distance from the orifice-section central axis, the occlusion section is shaped so as to define an occlusion-section curve that winds at least 2 turns around an occlusion-section central axis at a changing distance from the occlusion-section central axis, the connecting section connects the orifice-section curve with the occlusion-section curve, the orifice-section curve defines an orifice-section central opening having an orifice-section-central-opening cross-sectional area equal to at least 2% of an overall-orifice-section cross-sectional area of the orifice-section curve defined by an outermost loop of the orifice-section curve, the orifice-section-central-opening cross-sectional area and the overall-orifice-section cross-sectional area measured perpendicular to the orifice-section central axis, the orifice-section central axis and the occlusion-section central axis are not coaxial, and a projection of the occlusion-section curve occludes at least 25% of the orifice-section-central-opening cross-sectional area, wherein the projection of the occlusion-section curve is in a direction along the orifice-section central axis, onto an orifice-section plane perpendicular to the orifice-section central axis.

For some applications, the apparatus is configured such that, when the apparatus is unconstrained, the projection of the occlusion-section curve occludes at least 50% of the orifice-section-central-opening cross-sectional area.

For some applications, the apparatus is configured such that, when the apparatus is unconstrained, the orifice-section-central-opening cross-sectional area equals at least 3% of the overall-orifice-section cross-sectional area.

For some applications, the apparatus is configured such that, when the apparatus is unconstrained, the occlusion-section curve winds a number of turns around the occlusion-section central axis, the number of turns equal to at least 0.5 turns less than a number of turns that the orifice-section curve winds around the orifice-section central axis.

For some applications, the apparatus is configured such that, when the apparatus is unconstrained, the occlusion-section curve defines an occlusion-section central opening having an occlusion-section-central-opening cross-sectional area equal to at least 2% of an overall-occlusion-section cross-sectional area of the occlusion-section curve defined by an outermost loop of the occlusion-section curve, the occlusion-section-central-opening cross-sectional area and the overall-occlusion-section cross-sectional area measured perpendicular to the occlusion-section central axis.

For some applications, the apparatus is configured such that, when the apparatus is unconstrained, the occlusion-section central axis does not pass through the orifice-section central opening.

For some applications, the apparatus is configured such that, when the apparatus is unconstrained, the occlusion-section curve has an occlusion-section outermost diameter equal to between 50% and 150% of an orifice-section outermost diameter of the orifice-section curve.

For some applications, the apparatus is configured such that, when the apparatus is unconstrained, the connecting section is straight or has an average radius of curvature that is different from an average radius of curvature of the outermost loop of the orifice-section curve.

For some applications, the apparatus is configured such that, when the apparatus is unconstrained, the connecting section connects the outermost loop of the orifice-section curve with the orifice-section curve.

For some applications, the apparatus includes a wire that is shaped so as to define the orifice section, the occlusion section, and the connecting section.

For some applications, the apparatus is configured such that, when the apparatus is unconstrained, the orifice-section-central-opening cross-sectional area is at least 0.25 mm2.

For some applications, the apparatus is configured such that, when the apparatus is unconstrained, the occlusion-section-central-opening cross-sectional area is at least 0.25 mm2.

For some applications, the orifice section, the occlusion section, and the connecting section include one or more shape memory alloys.

For some applications, the orifice section, the occlusion section, and the connecting section include one or more superelastic alloys.

For any of the applications described hereinabove, the apparatus may be configured such that, when the apparatus is unconstrained, the orifice-section plane is parallel with or defines an angle of less than 30 degrees with an occlusion-section plane perpendicular to the occlusion-section central axis. For some applications, the apparatus is configured such that, when the apparatus is unconstrained, the orifice-section plane is parallel with or defines an angle of less than 15 degrees with the occlusion-section plane. For some applications, the apparatus is configured such that, when the apparatus is unconstrained, the orifice-section plane is parallel with the occlusion-section plane.

For any of the applications described hereinabove, the apparatus may be configured such that, when the apparatus is unconstrained, a distance between a center of mass of the orifice-section curve and a center of mass of the occlusion-section curve, measured along the orifice-section central axis, is between 20% and 80% of an orifice-section outermost diameter of the orifice-section curve. For some applications, the apparatus is configured such that, when the apparatus is unconstrained, the distance is between 25% and 75% of the orifice-section outermost diameter.

For any of the applications described hereinabove, the apparatus may be configured such that, when the apparatus is unconstrained, a distance between a geometric center of the orifice-section central opening and the occlusion-section curve, measured along the orifice-section central axis, is between 20% and 80% of an orifice-section outermost diameter of the orifice-section curve. For some applications, the apparatus is configured such that, when the apparatus is unconstrained, the distance is between 25% and 75% of the orifice-section outermost diameter.

For any of the applications described hereinabove, the apparatus may be configured such that, when the apparatus is unconstrained, the orifice-section central axis and the occlusion-section central axis are parallel to each other. For some applications, the apparatus is configured such that, when the apparatus is unconstrained, the orifice-section central axis and the occlusion-section central axis are at a distance from each other of between 20% and 80% of an orifice-section outermost diameter of the orifice-section curve.

For any of the applications described hereinabove, the apparatus may be configured such that, when the apparatus is unconstrained, the orifice-section curve is a three-dimensional curve. For some applications, the apparatus is configured such that, when the apparatus is unconstrained, the three-dimensional curve is a conical spiral.

For any of the applications described hereinabove, the apparatus may be configured such that, when the apparatus is unconstrained, an orifice-section outermost diameter of the orifice-section curve is between 2 and 10 mm. For some applications, the apparatus is configured such that, when the apparatus is unconstrained, the orifice-section outermost diameter is between 4 and 7 mm.

For any of the applications described hereinabove, the apparatus may be configured such that, when the apparatus is unconstrained, an occlusion-section outermost diameter of the occlusion-section curve is between 3 and 10 mm. For some applications, the apparatus is configured such that, when the apparatus is unconstrained, the occlusion-section outermost diameter is between 4 and 8 mm.

For any of the applications described hereinabove, a kit may be provided that includes the apparatus and a micro-catheter in which the apparatus is removably disposed for delivery to the vascular malformation. For some applications, the occlusion section is disposed more distally in the microcatheter than is the connecting section, which in turn is disposed more distally than is the orifice section. For some applications, the kit further includes a pusher tube, which is removably disposed in the microcatheter with a distal end of the pusher tube removably coupled to a proximal end of the orifice section.

There is further provided, in accordance with an application of the present invention, a method for treating a vascular malformation, the method including:

implanting (a) an occlusion section of an apparatus within the vascular malformation, (b) a connecting section of the apparatus, and (c) an orifice section of the apparatus within a portion of the vascular malformation so as to partially cover an orifice of the vascular malformation, the portion of the vascular malformation including one or more anatomical features selected from the group consisting of: a neck of the vascular malformation and a wall of the vascular malformation, such that:

the orifice section is shaped so as to define an orifice-section curve that winds at least 2.5 turns around an orifice-section central axis at a changing distance from the orifice-section central axis, the occlusion section is shaped so as to define an occlusion-section curve that winds at least 2 turns around an occlusion-section central axis at a changing distance from the occlusion-section central axis, the connecting section connects the orifice-section curve with the occlusion-section curve, the orifice-section curve defines an orifice-section central opening having an orifice-section-central-opening cross-sectional area equal to at least 2% of an overall-orifice-section cross-sectional area of the orifice-section curve defined by an outermost loop of the orifice-section curve, the orifice-section-central-opening cross-sectional area and the overall-orifice-section cross-sectional area measured perpendicular to the orifice-section central axis, the orifice-section central axis and the occlusion-section central axis are not coaxial, and a projection of the occlusion-section curve occludes at least 25% of the orifice-section-central-opening cross-sectional area, wherein the projection of the occlusion-section curve is in a direction along the orifice-section central axis, onto an orifice-section plane perpendicular to the orifice-section central axis.

For some applications, implanting the occlusion section, the connecting section, and the orifice section includes:

inserting the occlusion section, the connecting section, and the orifice section into a blood vessel while removably disposed in a microcatheter;

deploying the occlusion section from the microcatheter into the vascular malformation;

deploying the connecting section from the microcatheter; and deploying the orifice section from the microcatheter within the portion of the vascular malformation.

For some applications, deploying the occlusion section, the connecting section, and the orifice section includes deploying the occlusion section, thereafter deploying the connecting section, and thereafter deploying the orifice section.

For some applications, inserting the occlusion section, the connecting section, and the orifice section into the blood vessel includes pushing the orifice section distally using a pusher tube that is removably disposed in the microcatheter with a distal end of the pusher tube removably coupled to a proximal end of the orifice section.

For some applications, the vascular malformation is an aneurysm, and implanting the occlusion section includes implanting the occlusion section within the aneurysm.

For some applications, the apparatus is configured such that, when the apparatus is unconstrained, the projection of the occlusion-section curve occludes at least 50% of the orifice-section-central-opening cross-sectional area.

There is still further provided, in accordance with an application of the present invention, apparatus for treating a vascular malformation, the apparatus including:

an orifice section;

an intra-vascular-malformation docking section; and a connecting section, wherein the apparatus is configured such that, when unconstrained:

the orifice section is shaped so as to define an orifice-section curve that winds at least 2.5 turns around an orifice-section central axis at a changing distance from the orifice-section central axis, the intra-vascular-malformation docking section is shaped so as to define a docking-section curve that winds between 0.5 and 2 turns around a docking-section central axis at a changing or constant distance from the docking-section central axis, and the connecting section connects the orifice-section curve with the docking-section curve, and has an average radius of curvature that is different from an average radius of curvature of an outermost loop of the orifice-section curve.

For some applications, the apparatus is configured such that, when the apparatus is unconstrained:

a connecting-section slope of the connecting section equals the quotient of (a) a rise distance between the two endpoints of the connecting section, measured along the orifice-section central axis, divided by (b) a run distance equal to a length of the connecting section between the two endpoints of the connecting section, measured along the connecting section, an orifice-section slope of the orifice section equals the quotient of (a) a rise distance between the two endpoints of the orifice section, measured along the orifice-section central axis, divided by (b) a run distance equal to a length of the orifice section between the two endpoints of the orifice section, measured along the orifice section, and the connecting-section slope is greater than the orifice-section slope.

For some applications, the apparatus is configured such that, when the apparatus is unconstrained:

a connecting-section slope of the connecting section equals the quotient of (a) a rise distance between the two endpoints of the connecting section, measured along the orifice-section central axis, divided by (b) a run distance equal to a length of the connecting section between the two endpoints of the connecting section, measured along the connecting section, and the connecting-section slope is greater than 10%.

For some applications, the apparatus is configured such that, when the apparatus is unconstrained, the connecting section has a length of at least 15% of an orifice-section outermost diameter of the orifice-section curve.

For some applications, the apparatus is configured such that, when the apparatus is unconstrained, the length of the connecting section is no more than 90% of the orifice-section outermost diameter.

For some applications, the apparatus is configured such that, when the apparatus is unconstrained, the average radius of curvature of the connecting section is greater than the average radius of curvature of the outermost loop of the orifice-section curve.

For some applications, the apparatus is configured such that, when the apparatus is unconstrained, the average radius of curvature of the connecting section is at least 1 mm.

For some applications, the apparatus is configured such that, when the apparatus is unconstrained, the average radius of curvature of the connecting section equals at least 50% of the orifice-section outermost diameter.

For some applications, the apparatus is configured such that, when the apparatus is unconstrained, the connecting section connects the outermost loop of the orifice-section curve with the docking-section curve.

For some applications, the apparatus is configured such that, when the apparatus is unconstrained, the docking-section curve has a docking-section outermost diameter equal to between 15% and 80% of an orifice-section outermost diameter of the orifice-section curve.

For some applications, the apparatus is configured such that, when the apparatus is unconstrained, the docking-section outermost diameter equals between 25% to 50% of the orifice-section outermost diameter.

For some applications, the apparatus is configured such that, when the apparatus is unconstrained, the docking-section curve has a docking-section outermost diameter equal to between 100% and 150% of an orifice-section outermost diameter of the orifice-section curve.

For some applications, the apparatus is configured such that, when the apparatus is unconstrained, the docking-section curve has between 0.75 and 2 turns.

For some applications, the apparatus is configured such that, when the apparatus is unconstrained, the docking-section curve has between 1 and 2 turns.

For some applications, the apparatus is configured such that, when the apparatus is unconstrained, the docking-section curve has between 0.5 and 1.25 turns.

For some applications, the apparatus is configured such that, when the apparatus is unconstrained, the docking-section curve has between 0.75 and 1.25 turns.

For some applications, the apparatus is configured such that, when the apparatus is unconstrained, the docking-section curve has between 0.9 and 1.1 turns.

For some applications, the apparatus is configured such that, when the apparatus is unconstrained, the docking-section curve has between 1 and 1.1 turns.

For some applications, the apparatus is configured such that, when the apparatus is unconstrained, the connecting section is straight.

For some applications, the apparatus is configured such that, when the apparatus is unconstrained, a closest distance between the orifice-section curve and the docking-section curve, measured along the orifice-section central axis, is between 4% and 100% of an orifice-section outermost diameter of the orifice-section curve.

For some applications, the apparatus is configured such that, when the apparatus is unconstrained, the closest distance is between 4% and 50%.

For some applications, the apparatus is configured such that, when the apparatus is unconstrained, a distance between a center of mass of the orifice-section curve and a center of mass of the docking-section curve, measured along the orifice-section central axis, is between 7% and 100% of an orifice-section outermost diameter of the orifice-section curve.

For some applications, the apparatus is configured such that, when the apparatus is unconstrained, the distance is between 10% and 50% of the orifice-section outermost diameter.

For some applications, the apparatus is configured such that, when the apparatus is unconstrained, an orifice-section plane perpendicular to the orifice-section central axis is parallel with or defines an angle of less than 30 degrees with a docking-section plane perpendicular to the docking-section central axis.

For some applications, the apparatus is configured such that, when the apparatus is unconstrained, the orifice-section plane is parallel with the docking-section plane.

For some applications, the apparatus is configured such that, when the apparatus is unconstrained, the orifice-section central axis and the docking-section central axis are coaxial or at a distance from each other of less than 50% of an orifice-section outermost diameter of the orifice-section curve.

For some applications, the apparatus is configured such that, when the apparatus is unconstrained, an orifice-section plane perpendicular to the orifice-section central axis defines an angle of greater than 60 degrees with a docking-section plane perpendicular to the docking-section central axis.

For some applications, the apparatus is configured such that, when the apparatus is unconstrained, the angle is greater than 75 degrees.

For some applications, the apparatus is configured such that, when the apparatus is unconstrained, an orifice-section plane perpendicular to the orifice-section central axis defines an angle of between 30 and 60 degrees with a docking-section plane perpendicular to the docking-section central axis.

For some applications, the apparatus includes a wire that is shaped so as to define the orifice section, the intra-vascular-malformation docking section, and the connecting section, when the apparatus is unconstrained.

For some applications, the apparatus is configured such that, when the apparatus is unconstrained, the orifice-section curve is a three-dimensional curve.

For some applications, the apparatus is configured such that, when the apparatus is unconstrained, the three-dimensional curve is a conical spiral.

For some applications, the apparatus is configured such that, when the apparatus is unconstrained, an orifice-section outermost diameter of the orifice-section curve is between 2 and 10 mm.

For some applications, the apparatus is configured such that, when the apparatus is unconstrained, the orifice-section outermost diameter is between 4 and 7 mm.

For some applications, the apparatus is configured such that, when the apparatus is unconstrained, the docking-section curve winds around the docking-section central axis at the constant distance from the docking-section central axis.

For some applications, the apparatus is configured such that, when the apparatus is unconstrained, the orifice-section curve defines a central opening having an orifice-section-central-opening cross-sectional area equal to at least 2% of an overall-orifice-section cross-sectional area of the orifice-section curve defined by the outermost loop of the orifice-section curve, the orifice-section-central-opening cross-sectional area and the overall-orifice-section cross-sectional area measured perpendicular to the orifice-section central axis.

For some applications, the apparatus is configured such that, when the apparatus is unconstrained, the orifice-section curve defines a central opening having an orifice-section-central-opening cross-sectional area of at least 0.25 mm2.

For some applications, the orifice section, the intra-vascular-malformation docking section, and the connecting section include one or more shape memory alloys.

For some applications, the orifice section, the intra-vascular-malformation docking section, and the connecting section include one or more superelastic alloys.

For any of the applications described hereinabove, a kit may be provided that includes the apparatus and a microcatheter in which the apparatus is removably disposed for delivery to the vascular malformation. For some applications, the intra-vascular-malformation docking section is disposed more distally in the microcatheter than is the connecting section, which in turn is disposed more distally than is the orifice section. For some applications, the kit further includes a pusher tube, which is removably disposed in the microcatheter with a distal end of the pusher tube removably coupled to a proximal end of the orifice section.

There is additionally provided, in accordance with an application of the present invention, a method for treating a vascular malformation, the method including:

implanting (a) an intra-vascular-malformation docking section of an apparatus within the vascular malformation, (b) a connecting section of the apparatus, and (c) an orifice section of the apparatus within a portion of the vascular malformation so as to at least partially cover an orifice of the vascular malformation, the portion of the vascular malformation including one or more anatomical features selected from the group consisting of: a neck of the vascular malformation and a wall of the vascular malformation, such that:

the orifice section is shaped so as to define an orifice-section curve that winds at least 2.5 turns around an orifice-section central axis at a changing distance from the orifice-section central axis, the intra-vascular-malformation docking section is shaped so as to define a docking-section curve that winds between 0.5 and 2 turns around a docking-section central axis at a changing or constant distance from the docking-section central axis, and the connecting section connects the orifice-section curve with the docking-section curve, and has an average radius of curvature that is different from an average radius of curvature of an outermost loop of the orifice-section curve; and implanting endovascular embolization coils in the vascular malformation such that the endovascular embolization coils become entangled with the intra-vascular-malformation docking section.

For some applications, implanting the intra-vascular-malformation docking section, the connecting section, and the orifice section includes:

inserting the intra-vascular-malformation docking section, the connecting section, and the orifice section into a blood vessel while removably disposed in a microcatheter;

deploying the intra-vascular-malformation docking section from the microcatheter into the vascular malformation;

deploying the connecting section from the microcatheter; and deploying the orifice section from the microcatheter within the portion of the vascular malformation.

For some applications, deploying the intra-vascular-malformation docking section, the connecting section, and the orifice section includes deploying the intra-vascular-malformation docking section, thereafter deploying the connecting section, and thereafter deploying the orifice section.

For some applications, inserting the intra-vascular-malformation docking section, the connecting section, and the orifice section into the blood vessel includes pushing the orifice section distally using a pusher tube that is removably disposed in the microcatheter with a distal end of the pusher tube removably coupled to a proximal end of the orifice section.

For some applications, the vascular malformation is an aneurysm, and implanting the intra-vascular-malformation docking section includes implanting the intra-vascular-malformation docking section within the aneurysm.

For some applications, the apparatus is configured such that, when the apparatus is unconstrained:

a connecting-section slope of the connecting section equals the quotient of (a) a rise distance between the two endpoints of the connecting section, measured along the orifice-section central axis, divided by (b) a run distance equal to a length of the connecting section between the two endpoints of the connecting section, measured along the connecting section, an orifice-section slope of the orifice section equals the quotient of (a) a rise distance between the two endpoints of the orifice section, measured along the orifice-section central axis, divided by (b) a run distance equal to a length of the orifice section between the two endpoints of the orifice section, measured along the orifice section, and the connecting-section slope is greater than the orifice-section slope.

For some applications, the apparatus is configured such that, when the apparatus is unconstrained:

a connecting-section slope of the connecting section equals the quotient of (a) a rise distance between the two endpoints of the connecting section, measured along the orifice-section central axis, divided by (b) a run distance equal to a length of the connecting section between the two endpoints of the connecting section, measured along the connecting section, and the connecting-section slope is greater than 10%.

For some applications, the apparatus is configured such that, when the apparatus is unconstrained, the connecting section has a length of at least 15% of an orifice-section outermost diameter of the orifice-section curve.

For some applications, the apparatus is configured such that, when the apparatus is unconstrained, the length of the connecting section is no more than 90% of the orifice-section outermost diameter.

For some applications, the apparatus is configured such that, when the apparatus is unconstrained, the average radius of curvature of the connecting section is greater than the average radius of curvature of the outermost loop of the orifice-section curve.

For some applications, the apparatus is configured such that, when the apparatus is unconstrained, the average radius of curvature of the connecting section is at least 1 mm.

For some applications, the apparatus is configured such that, when the apparatus is unconstrained, the average radius of curvature of the connecting section equals at least 50% of the orifice-section outermost diameter.

For some applications, the apparatus is configured such that, when the apparatus is unconstrained, the connecting section connects the outermost loop of the orifice-section curve with the docking-section curve.

For some applications, the apparatus is configured such that, when the apparatus is unconstrained, the docking-section curve has a docking-section outermost diameter equal to between 15% and 80% of an orifice-section outermost diameter of the orifice-section curve.

For some applications, the apparatus is configured such that, when the apparatus is unconstrained, the docking-section outermost diameter equals between 25% to 50% of the orifice-section outermost diameter.

For some applications, the apparatus is configured such that, when the apparatus is unconstrained, the docking-section curve has a docking-section outermost diameter equal to between 100% and 150% of an orifice-section outermost diameter of the orifice-section curve.

For some applications, the apparatus is configured such that, when the apparatus is unconstrained, the docking-section curve has between 0.75 and 2 turns.

For some applications, the apparatus is configured such that, when the apparatus is unconstrained, the docking-section curve has between 1 and 2 turns.

For some applications, the apparatus is configured such that, when the apparatus is unconstrained, the docking-section curve has between 0.5 and 1.25 turns.

For some applications, the apparatus is configured such that, when the apparatus is unconstrained, the docking-section curve has between 0.75 and 1.25 turns.

For some applications, the apparatus is configured such that, when the apparatus is unconstrained, the docking-section curve has between 0.9 and 1.1 turns.

For some applications, the apparatus is configured such that, when the apparatus is unconstrained, the docking-section curve has between 1 and 1.1 turns.

For some applications, the apparatus is configured such that, when the apparatus is unconstrained, the connecting section is straight.

For some applications, the apparatus is configured such that, when the apparatus is unconstrained, a closest distance between the orifice-section curve and the docking-section curve, measured along the orifice-section central axis, is between 4% and 100% of an orifice-section outermost diameter of the orifice-section curve.

For some applications, the apparatus is configured such that, when the apparatus is unconstrained, the closest distance is between 4% and 50%.

For some applications, the apparatus is configured such that, when the apparatus is unconstrained, a distance between a center of mass of the orifice-section curve and a center of mass of the docking-section curve, measured along the orifice-section central axis, is between 7% and 100% of an orifice-section outermost diameter of the orifice-section curve.

For some applications, the apparatus is configured such that, when the apparatus is unconstrained, the distance is between 10% and 50% of the orifice-section outermost diameter.

For some applications, the apparatus is configured such that, when the apparatus is unconstrained, an orifice-section plane perpendicular to the orifice-section central axis is parallel with or defines an angle of less than 30 degrees with a docking-section plane perpendicular to the docking-section central axis.

For some applications, the apparatus is configured such that, when the apparatus is unconstrained, the orifice-section plane is parallel with the docking-section plane.

For some applications, the apparatus is configured such that, when the apparatus is unconstrained, the orifice-section central axis and the docking-section central axis are coaxial or at a distance from each other of less than 50% of an orifice-section outermost diameter of the orifice-section curve.

For some applications, the apparatus is configured such that, when the apparatus is unconstrained, an orifice-section plane perpendicular to the orifice-section central axis defines an angle of greater than 60 degrees with a docking-section plane perpendicular to the docking-section central axis.

For some applications, the apparatus is configured such that, when the apparatus is unconstrained, the angle is greater than 75 degrees.

For some applications, the apparatus is configured such that, when the apparatus is unconstrained, an orifice-section plane perpendicular to the orifice-section central axis defines an angle of between 30 and 60 degrees with a docking-section plane perpendicular to the docking-section central axis.

For some applications, the apparatus includes a wire that is shaped so as to define the orifice section, the intravascular-malformation docking section, and the connecting section, when the apparatus is unconstrained.

For some applications, the apparatus is configured such that, when the apparatus is unconstrained, the orifice-section curve is a three-dimensional curve.

For some applications, the apparatus is configured such that, when the apparatus is unconstrained, the three-dimensional curve is a conical spiral.

For some applications, the apparatus is configured such that, when the apparatus is unconstrained, an orifice-section outermost diameter of the orifice-section curve is between 2 and 10 mm.

For some applications, the apparatus is configured such that, when the apparatus is unconstrained, the orifice-section outermost diameter is between 4 and 8 mm.

For some applications, the apparatus is configured such that, when the apparatus is unconstrained, the docking-section curve winds around the docking-section central axis at the constant distance from the docking-section central axis.

For some applications, the apparatus is configured such that, when the apparatus is unconstrained, the orifice-section curve defines a central opening having an orifice-section-central-opening cross-sectional area equal to at least 2% of an overall-orifice-section cross-sectional area of the orifice-section curve defined by the outermost loop of the orifice-section curve, the orifice-section-central-opening cross-sectional area and the overall-orifice-section cross-sectional area measured perpendicular to the orifice-section central axis.

For some applications, the apparatus is configured such that, when the apparatus is unconstrained, the orifice-section curve defines a central opening having an orifice-section-central-opening cross-sectional area of at least 0.25 mm2.

For some applications, the orifice section, the intravascular-malformation docking section, and the connecting section include one or more shape memory alloys.

For some applications, the orifice section, the intra-vascular-malformation docking section, and the connecting section include one or more superelastic alloys.

The present invention will be more fully understood from the following detailed description of embodiments thereof, taken together with the drawings, in which:

BRIEF DESCRIPTION OF THE DRAWINGS

FIGS. 6A-E are schematic illustrations of a method for deploying the apparatus of FIGS. 1A-D to treat a vascular malformation, in accordance with an application of the present invention;

FIGS. 7A-B are schematic illustrations of another apparatus for treating a vascular malformation, in accordance with an application of the present invention.

DETAILED DESCRIPTION OF APPLICATIONS

Figures 1A, 1B:
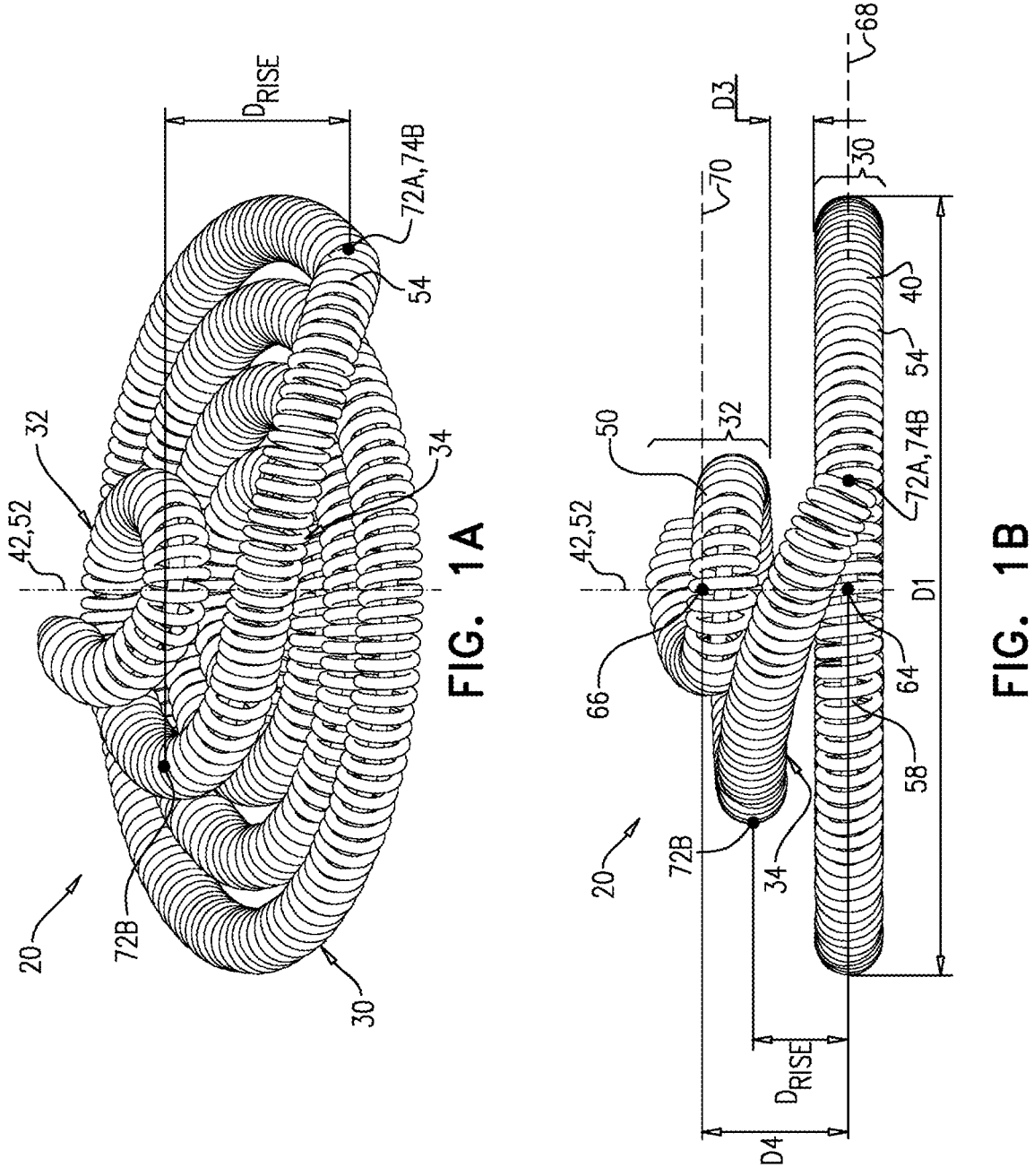
FIGS. 1A-D are schematic illustrations of apparatus for treating a vascular malformation, in accordance with an application of the present invention.

FIGS. 1A-D are schematic illustrations of apparatus 20 for treating a vascular malformation, in accordance with an application of the present invention. For some applications, apparatus 20 is configured to bridge the neck of a vascular malformation, such as an aneurysm, e.g., a wide-necked aneurysm, in order to prevent coil herniation, such as described in more detail hereinbelow with reference to FIGS. 6A-E. For example, the aneurysm may be a saccular aneurysm formed in the wall of a blood vessel, typically an artery, such as a cerebral aneurysm, a coronary artery aneurysm, a ventricular aneurysm, an aneurysm of the sinus of Valsalva, an aneurysm following cardiac surgery, or an aortic aneurysm. Alternatively, the vascular malformation may be any congenital and/or non-congenital blood vessel abnormality, such as, but not limited to, a fistula, a tumor, or an arteriovenous malformation.

Apparatus 20 comprises an orifice section 30, an intra-vascular-malformation docking section 32, and a connecting section 34. As described in more detail hereinbelow with reference to FIGS. 6A-E, orifice section 30 is configured to bridge the neck of the vascular malformation, which helps prevent coil herniation, i.e., endovascular embolization coils protruding from the aneurysm. Intra-vascular-malformation docking section 32 is configured to facilitate entanglement with endovascular embolization coils 210 (described hereinbelow with reference to FIG. 6E), which helps connect apparatus 20 with endovascular embolization coils 210 to create a single mass.

Apparatus 20 is typically configured such that, when unconstrained (by the patient's anatomy, a microcatheter, or otherwise):

orifice section 30 is shaped so as to define an orifice-section curve 40 (labeled in FIG. 1C) that winds at least 2 turns (typically at least 2.5 turns), and/or no more than 10 turns, such as between 2 (e.g., 2.5) and 10 turns, around an orifice-section central axis 42 (labeled in FIGS. 1B-D) at a changing distance from orifice-section central axis 42 (e.g., at a monotonically changing distance), intra-vascular-malformation docking section 32 is shaped so as to define a docking-section curve 50 (labeled in FIG. 1C) that winds between 0.5 and 2 turns (e.g., between 0.75 and 2 turns, such as between 1 and 2 turns, or between 0.5 and 1.25 turns, such as between 0.75 and 1.25 turns, e.g., between 0.9 and 1.1 turns, such as between 1 and 1.1 turns) around a docking-section central axis 52 (labeled in FIGS. 1B-D) at a changing or constant distance from docking-section central axis 52, and connecting section 34 connects orifice-section curve 40 with docking-section curve 50, and typically has an average radius of curvature that is different from an average radius of curvature of an outermost loop 60 (labeled in FIGS. 1C-D) of orifice-section curve 40.

Apparatus 20 typically also has the above-listed characteristics upon implantation in the vascular malformation, in part because the size of apparatus 20 is selected based on the size of the vascular malformation.

As used in the present application, a "turn" of a curve is a 360-degree turn of the curve around the central axis.

For some applications, orifice-section curve 40 is a three-dimensional curve when apparatus 20 is unconstrained. For some of these applications, the three-dimensional curve is a conical spiral when apparatus 20 is unconstrained.

For some applications, orifice-section curve 40 defines a central opening 62 (labeled in FIGS. 1C-D) having an orifice-section-central-opening cross-sectional area equal to at least 2% of an overall-orifice-section cross-sectional area of orifice-section curve 40 defined by outermost loop 60 (labeled in FIGS. 1C-D) of orifice-section curve 40, when apparatus 20 is unconstrained, the orifice-section-central-opening cross-sectional area and the overall-orifice-section cross-sectional area measured perpendicular to orifice-section central axis 42. Alternatively or additionally, for some applications, central opening 62 has an orifice-section-central-opening cross-sectional area of at least 0.25 mm2, when apparatus 20 is unconstrained.

For some applications, apparatus 20 comprises a wire 54 that is shaped so as to define orifice section 30, intra-vascular-malformation docking section 32, and connecting section 34. For some applications, as shown in the figures, wire 54 is micro-coiled so as to define a primary winding 56, such as about an internal wire 58 that may or may not run along the length of apparatus 20 (labeled in FIG. 2). The curves described herein are macro-curves and do not relate to this optional micro-coiling, but rather relate to the macro-structures described herein, such as orifice section 30 and connecting section 34. For some applications, orifice section 30, intra-vascular-malformation docking section 32, and connecting section 34 comprise one or more shape memory alloys and/or one or more superelastic alloys.

Figure 1C:
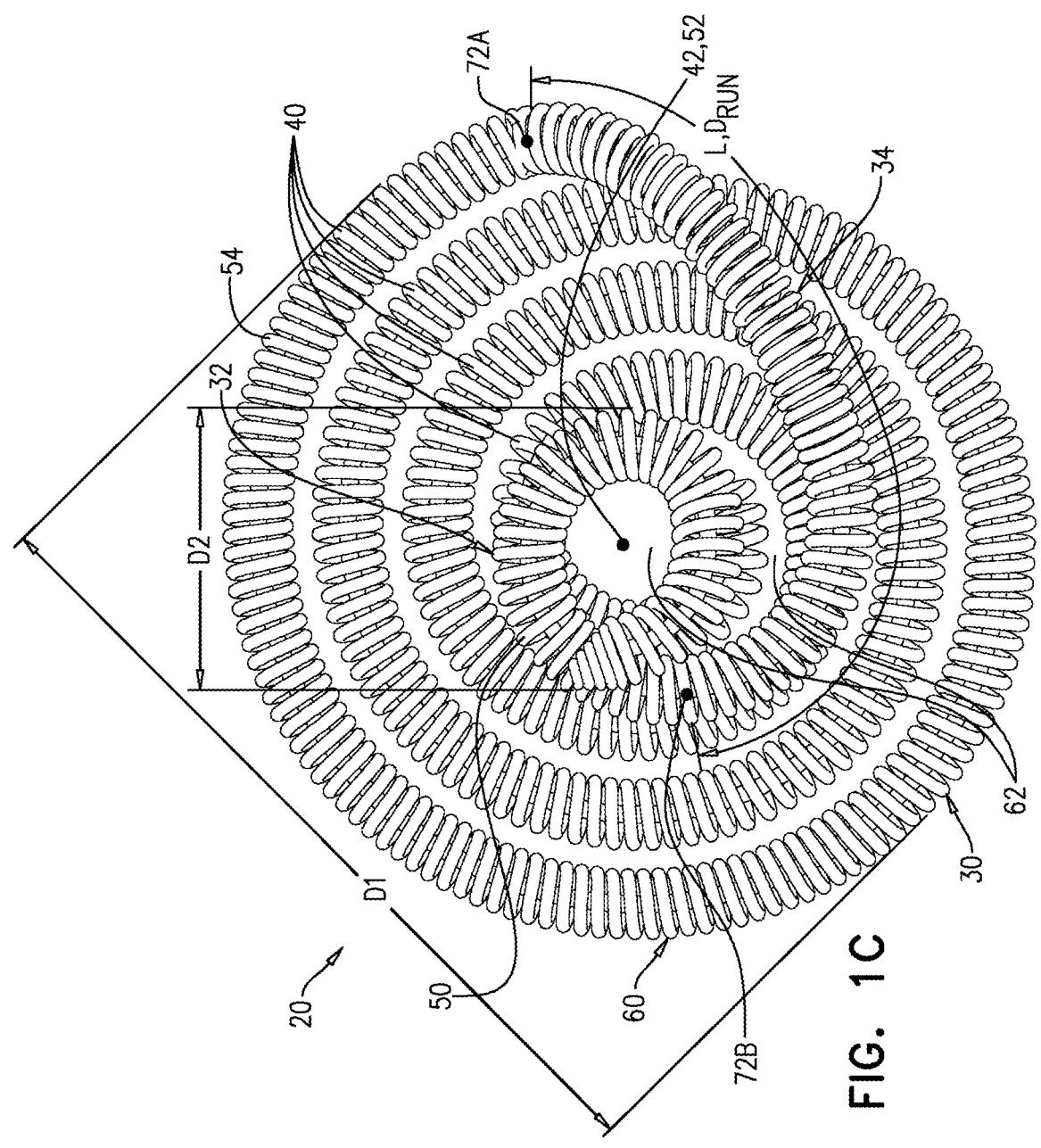
Figure 1D:
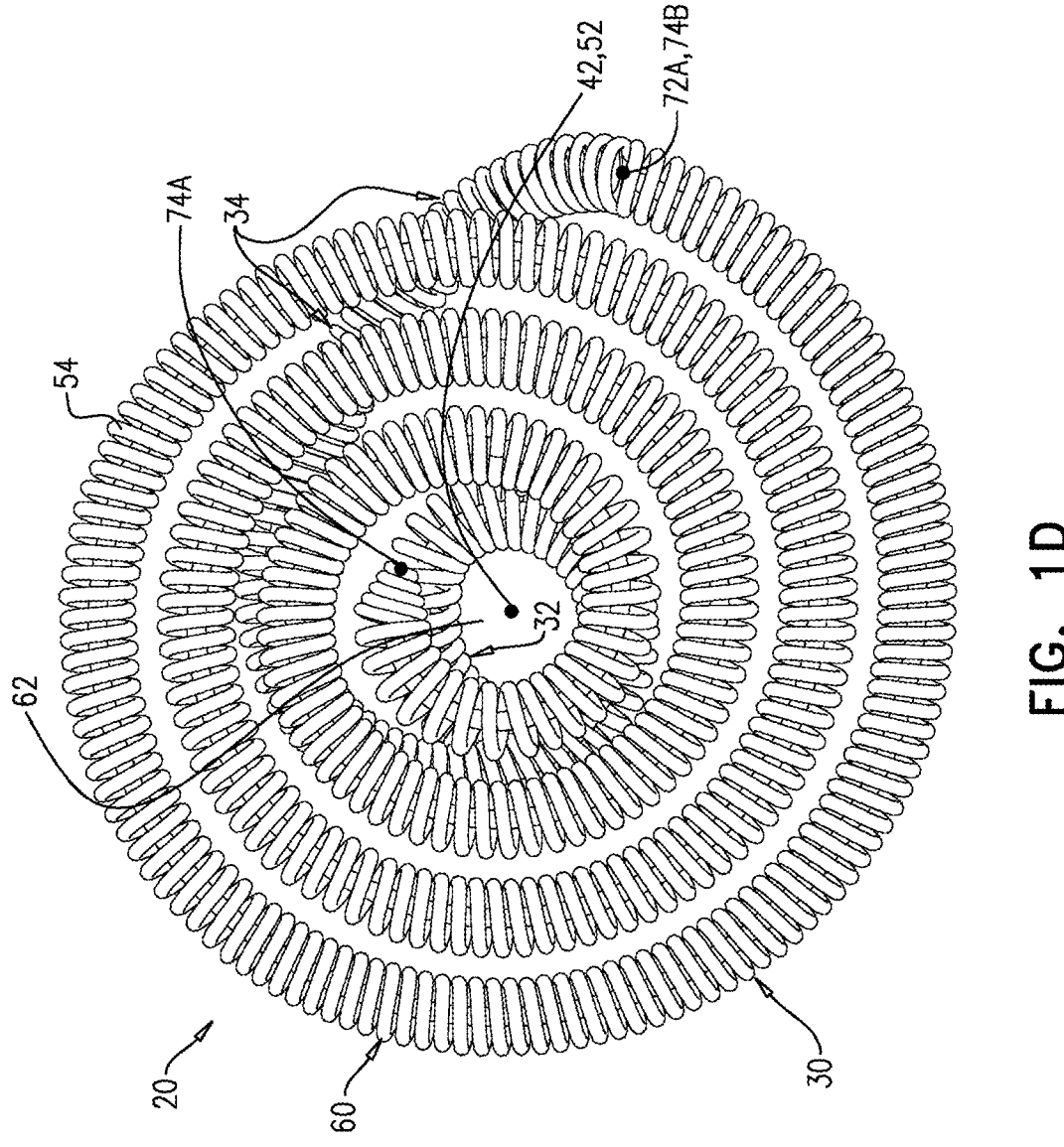

As labeled in FIGS. 1B and 1C, orifice-section curve 40 has an orifice-section outermost diameter D1. Typically, the orifice-section outermost diameter D1 is at least 2 mm (e.g., at least 4 mm), no more than 10 mm (e.g., no more than 8 mm, such as no more than 7 mm), and/or between 2 and 10 mm (e.g., between 2 and 8 mm, such as between 4 and 7 mm), when apparatus 20 is unconstrained.

As labeled in FIG. 1C, docking-section curve 50 has a docking-section outermost diameter D2. Typically, the docking-section outermost diameter D2 is at least 1 mm, no more than 10 mm, and/or between 1 and 10 mm.

For some applications, the docking-section outermost diameter D2 equals between 15% and 80%, such as between 25% and 50%, of the orifice-section outermost diameter D1 when apparatus 20 is unconstrained.

For some applications, as shown in the figures, connecting section 34 connects outermost loop 60 of orifice-section curve 40 with docking-section curve 50 when apparatus 20 is unconstrained. Alternatively, connecting section 34 connects an innermost loop of orifice-section curve 40 with docking-section curve 50 when apparatus 20 is unconstrained (configuration not shown).

As labeled in FIG. 1C, for some applications, connecting section 34 has a length L of at least 15% (e.g., at least 20%, such as at least 30%, e.g., at least 50%), no more than 90% (e.g., no more than 70%), and/or between 15% and 90% (e.g., between 50% and 70%, such as about 60%) of the orifice-section outermost diameter D1. In configurations in which connecting section 34 is curved, the length L is measured along the curvature of connecting section 34 (rather than in a straight line between the endpoints of connecting section 34).

Typically, connecting section 34 has an average radius of curvature that is different from an average radius of curvature of outermost loop 60 of orifice-section curve 40, when apparatus 20 is unconstrained. For example, the average radius of curvature of connecting section 34 may be greater than, such as greater than 100% of, the average radius of curvature of outermost loop 60 of orifice-section curve 40, when apparatus 20 is unconstrained; alternatively, the average radius of curvature of connecting section 34 is less than, such as less than 100% of, the average radius of curvature of outermost loop 60 of orifice-section curve 40, when apparatus 20 is unconstrained. Alternatively or additionally, for some applications, the average radius of curvature of connecting section 34 is at least 1 mm, such as at least 1.5 mm (e.g., at least 2 mm), when apparatus 20 is unconstrained (and, typically, connecting section 34 has a length L of at least 30% (e.g., at least 50%), no more than 90% (e.g., no more than 70%), and/or between 30% and 90% (e.g., between 50% and 70%, such as about 60%) of the orifice-section outermost diameter D1). Further alternatively or additionally, for some applications, connecting section 34 has an average radius of curvature equal to greater than 50% of the orifice-section outermost diameter D1 when apparatus 20 is unconstrained (and, typically, connecting section 34 has the length described immediately above).

For other applications, connecting section 34 is straight when apparatus 20 is unconstrained.

A connecting-section slope of connecting section 34 equals the quotient of:
- (a) a rise distance $D_{RISE}$ between the two endpoints 72A, 72B of connecting section 34, measured along orifice-section central axis 42 (the rise distance $D_{RISE}$ is measured between cross-sectional centroids of connecting section 34 at the two endpoints 72A, 72B), as labeled in FIGS. 1A and 1B, divided by
- (b) a run distance $D_{RUN}$ equal to the length L of connecting section 34 between the two endpoints 72A, 72B of connecting section 34, measured along connecting section 34; in configurations in which connecting section 34 is curved, the length L is measured along the curvature of connecting section 34 (rather than in a straight line between the endpoints 72A, 72B of connecting section 34), as labeled in FIG. 1C.

An orifice-section slope of orifice section 30 equals the quotient of:
- (a) a rise distance between the two endpoints 74A, 74B of the orifice section 30, measured along orifice-section central axis 42 (the rise distance is measured between cross-sectional centroids of orifice section 30 at the two endpoints 74A, 74B), divided by
- (b) a run distance equal to the length of orifice section 30 between the two endpoints 74A, 74B of orifice section 30, measured along orifice section 30; the length is measured along the curvature of orifice section 30 (rather than in a straight line between the endpoints 74A, 74B of orifice section 30).

By way of example and not limitation, the orifice-section slope of the configurations illustrated in the figures is zero.

Typically, the connecting-section slope is greater than the orifice-section slope when apparatus 20 is unconstrained. Alternatively or additionally, for some applications, the connecting-section slope is greater than 0.1 when apparatus 20 is unconstrained.

For some applications, as labeled in FIG. 1B, a closest distance D3 between orifice-section curve 40 and docking-section curve 50, measured along orifice-section central axis 42, is between 4% and 100%, such as between 4% (e.g., 5%) and 50%, e.g., between 4% (e.g., 5%) and 25%, of the orifice-section outermost diameter D1 when apparatus 20 is unconstrained. Alternatively or additionally, for some applications, as labeled in FIG. 1B, a distance D4 between a center of mass 64 of orifice-section curve 40 and a center of mass 66 of docking-section curve 50, measured along orifice-section central axis 42, is between 7% and 100%, such as between 10% and 100%, e.g., between 10% and 50%, of the orifice-section outermost diameter D1 when apparatus 20 is unconstrained.

For some applications, as labeled in FIG. 1B, an orifice-section plane 68 perpendicular to orifice-section central axis 42 is parallel with (such as shown in FIG. 1A-D) or defines an angle of less than 30 degrees with a docking-section plane 70 perpendicular to docking-section central axis 52, when apparatus 20 is unconstrained. For some of these applications, orifice-section central axis 42 and docking-section central axis 52 are coaxial (such as shown in FIG. 1A-D) or at a distance from each other of less than 50% (e.g., less than 25%) of the orifice-section outermost diameter D1 when apparatus 20 is unconstrained (configuration not shown).

Figures 2, 3:
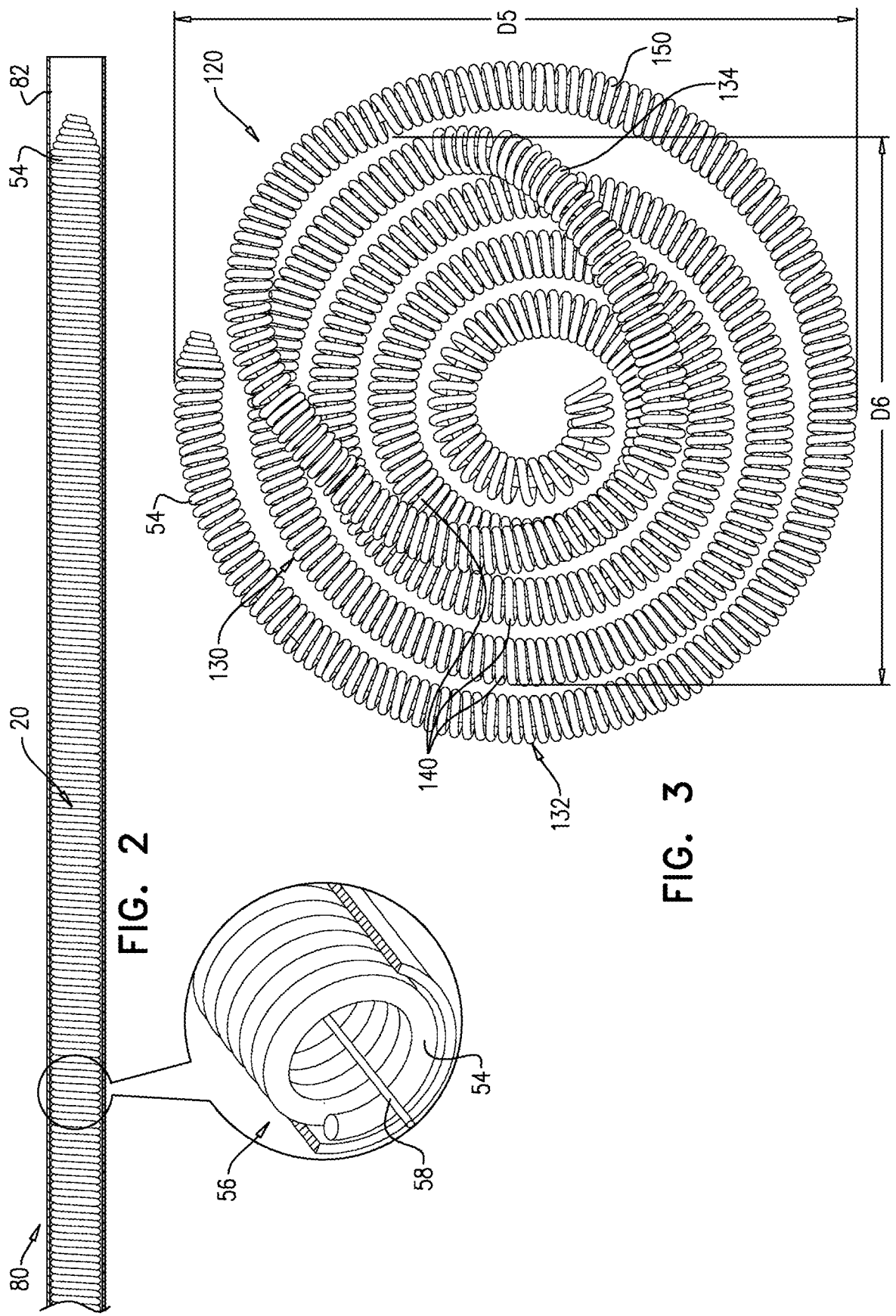
FIG. 2 is a schematic illustration of a kit, in accordance with an application of the present invention.
FIG. 3 is a schematic illustration of another apparatus for treating a vascular malformation, in accordance with an application of the present invention.

Reference is made to FIG. 2, which is a schematic illustration of a kit 80, in accordance with an application of the present invention. Kit 80 comprises apparatus 20 and a microcatheter 82 in which apparatus 20 is removably disposed for delivery to the vascular malformation.

Reference is made to FIG. 3, which is a schematic illustration of apparatus 120 for treating a vascular malformation, in accordance with an application of the present invention. Other than as described below, apparatus 120 is identical to apparatus 20 described hereinabove with reference to FIGS. 1A-2. A connecting section 134 connects an orifice-section curve 140 of an orifice section 130 with a docking-section curve 150 of an intra-vascular-malformation docking section 132, and typically has an average radius of curvature that is different from an average radius of curvature of an outermost loop of orifice-section curve 140. Docking-section curve 150 has a docking-section outermost diameter D5 equal to between 100% and 150% of an orifice-section outermost diameter D6 of orifice-section curve 140 when apparatus 20 is unconstrained.

Figures 4, 5:
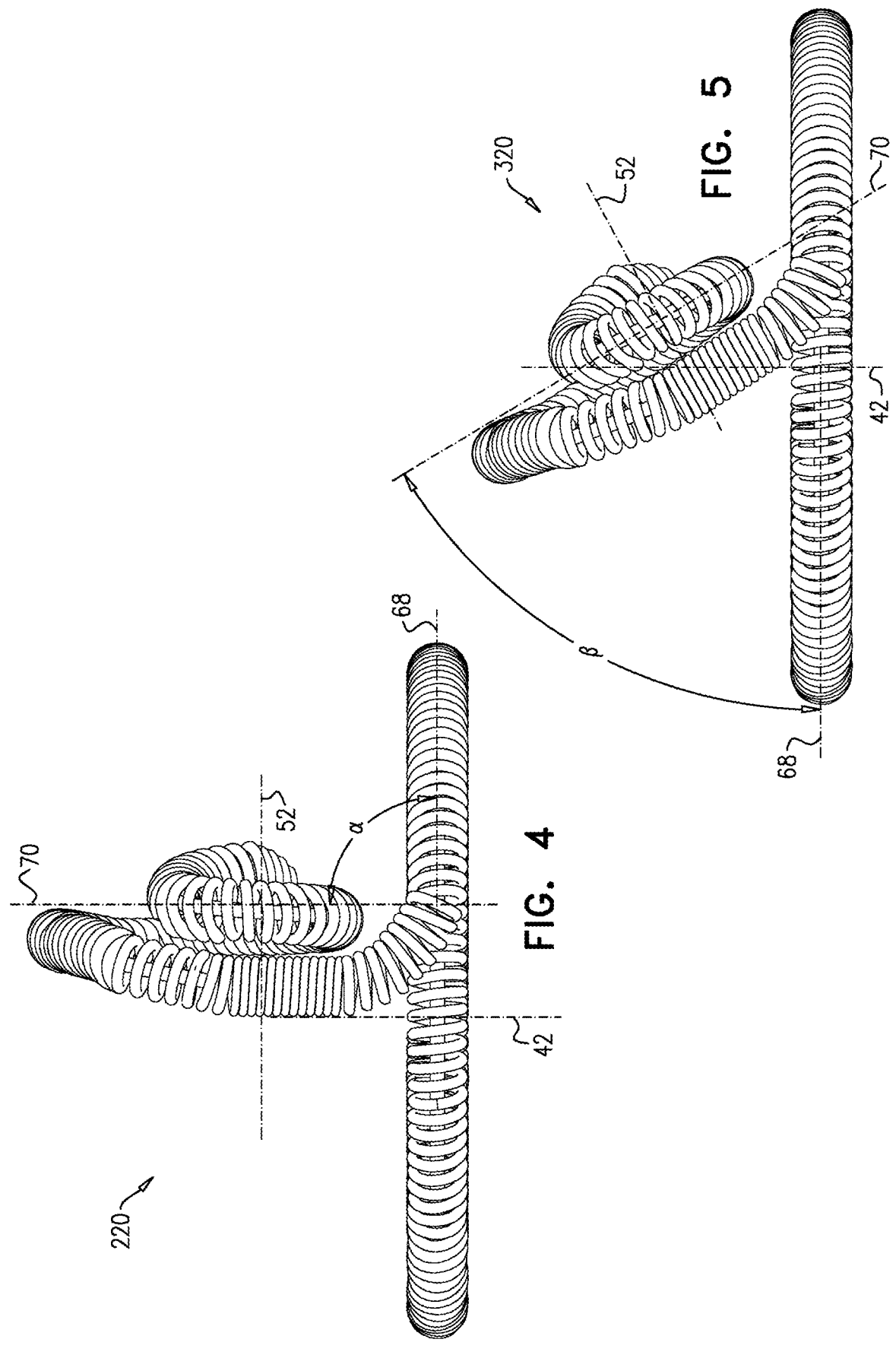
FIG. 4 is a schematic illustration of yet another apparatus for treating a vascular malformation, in accordance with an application of the present invention.
FIG. 5 is a schematic illustration of still another apparatus for treating a vascular malformation, in accordance with an application of the present invention.

Reference is made to FIG. 4, which is a schematic illustration of apparatus 220 for treating a vascular malformation, in accordance with an application of the present invention. Other than as described below, apparatus 220 is identical to apparatus 20 described hereinabove with reference to FIGS. 1A-2. In this configuration, orifice-section plane 68 defines an angle α (alpha) of greater than 60 degrees, such as greater than 75 degrees (e.g., 90 degrees) with docking-section plane 70 when apparatus 20 is unconstrained.

Reference is made to FIG. 5, which is a schematic illustration of apparatus 320 for treating a vascular malformation, in accordance with an application of the present invention. Other than as described below, apparatus 320 is identical to apparatus 20 described hereinabove with reference to FIGS. 1A-2. In this configuration, orifice-section plane 68 defines an angle β (beta) of between 30 and 60 degrees, such as between 40 and 50 degrees (e.g., 45 degrees) with docking-section plane 70 when apparatus 20 is unconstrained.

Reference is made to FIGS. 6A-E, which are schematic illustrations of a method for deploying apparatus 20 to treat a vascular malformation, such as an aneurysm 200, in accordance with an application of the present invention. The method may also be used to deploy apparatus 120, described hereinabove with reference to FIG. 3; apparatus 220, described hereinabove with reference to FIG. 4; or apparatus 320, described hereinabove with reference to FIG. 5.

Figures 6A, 6B:
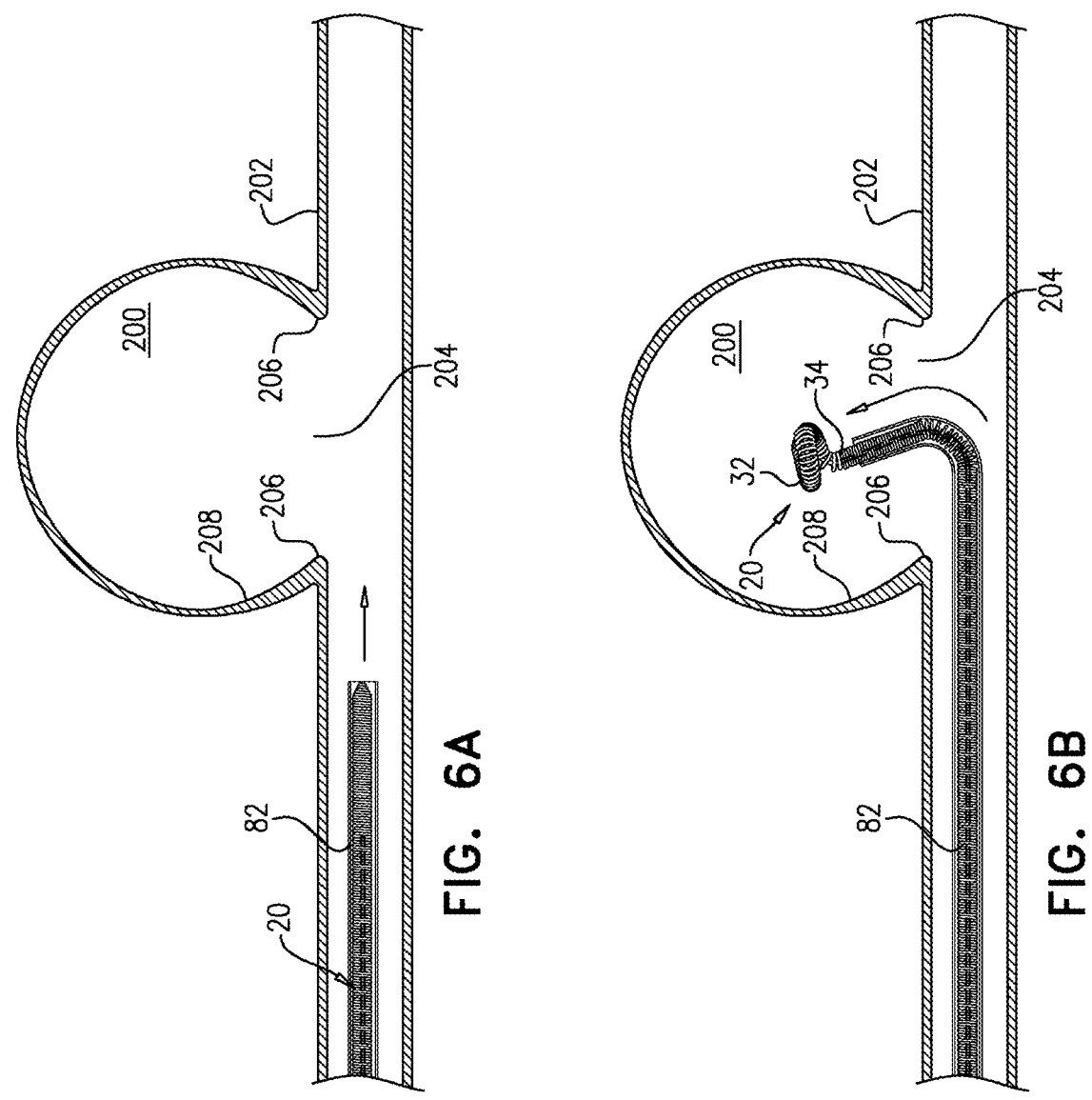

As shown in FIG. 6A, typically intra-vascular-malformation docking section 32, connecting section 34, and orifice section 30 are inserted into a blood vessel 202 while removably disposed in microcatheter 82. Typically, intra-vascular-malformation docking section 32 is disposed more distally in microcatheter 82 than is connecting section 34, which in turn is disposed more distally than is orifice section 30. Typically, a pusher tube 84 is removably disposed in microcatheter 82 with a distal end 86 of pusher tube 84 removably coupled to a proximal end 88 of orifice section 30, as labeled in FIG. 6C.

As shown in FIG. 6B, intra-vascular-malformation docking section 32 is deployed from microcatheter 82 into the vascular malformation, e.g., aneurysm 200.

As shown in FIG. 6C, connecting section 34 is deployed from microcatheter 82.

As shown in FIG. 6D, orifice section 30 is deployed from microcatheter 82 within a portion of the vascular malformation, e.g., aneurysm 200, so as to at least partially cover an orifice 204 of the vascular malformation, the portion of the vascular malformation including one or more anatomical features selected from the group consisting of: a neck 206 of the vascular malformation and a wall 208 of the vascular malformation.

Orifice section 30 is deployed such that:

orifice section 30 is shaped so as to define orifice-section curve 40 that winds at least 2.5 turns around orifice-section central axis 42 (labeled in FIGS. 1A-D) at a changing distance from orifice-section central axis 42 (e.g., at a monotonically changing distance), intra-vascular-malformation docking section 32 is shaped so as to define docking-section curve 50 (labeled in FIGS. 1B-C) that winds between 0.5 and 2 turns around docking-section central axis 52 at a changing or constant distance from docking-section central axis 52, and connecting section 34 connects orifice-section curve 40 with docking-section curve 50 (labeled in FIGS. 1B-C), and typically is straighter than orifice-section curve 40 and straighter than docking-section curve 50.

Figures 6E, 7A:
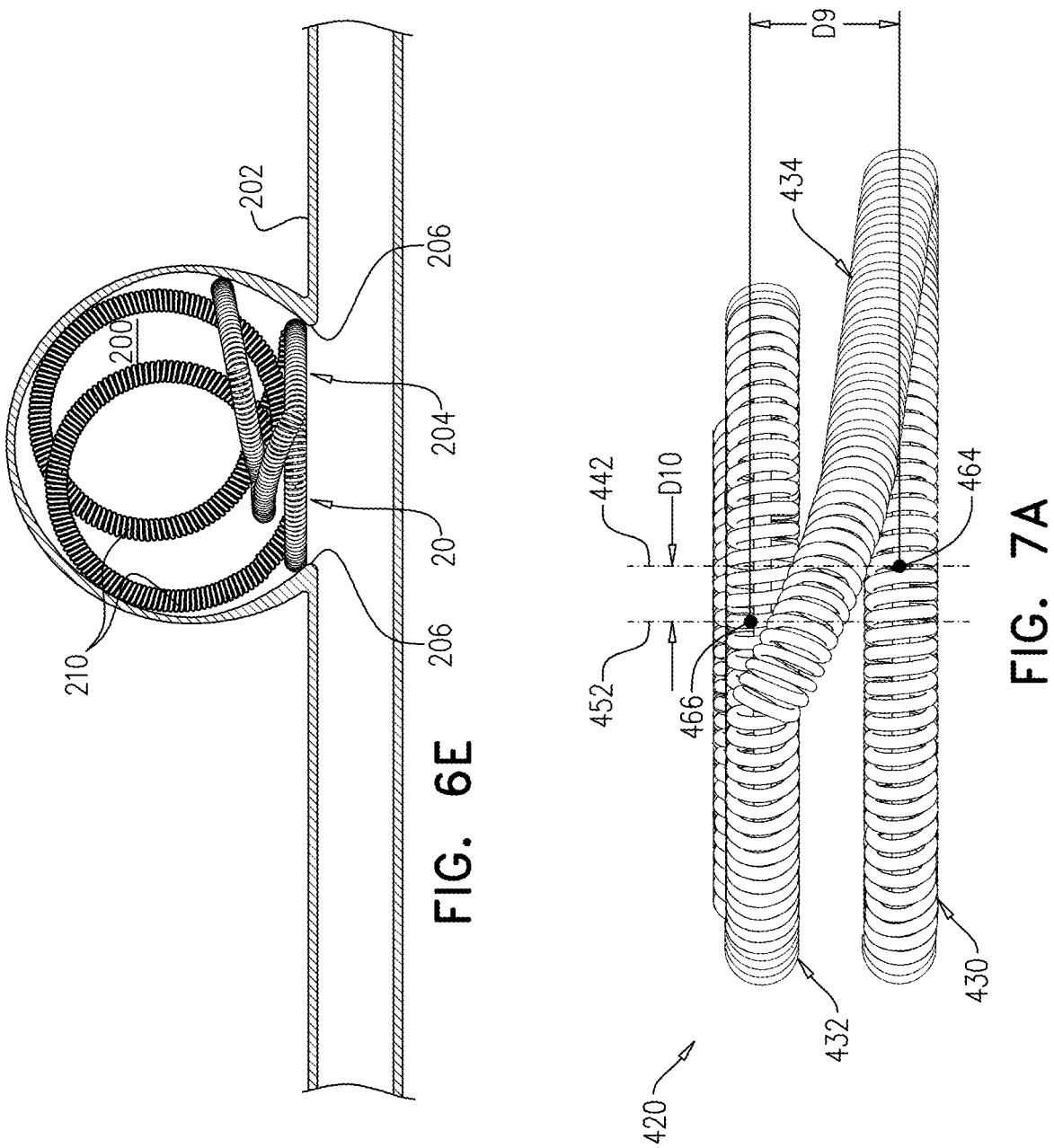

As shown in FIG. 6E, the method typically further comprises implanting endovascular embolization coils 210 in the vascular malformation, e.g., aneurysm 200, such that endovascular embolization coils 210 become entangled with intra-vascular-malformation docking section 32 (labeled in FIGS. 6B-D). Orifice section 30 reduces the risk of (typically prevents) coil herniation, i.e., endovascular embolization coils 210 exiting the vascular malformation into the parent vessel, particularly in malformations with a wide opening such as wide-neck aneurysms and/or those located at bifurcations. The anatomy of wide-neck aneurysms often does not allow the aneurysmal sac to retain endovascular embolization coils 210 by itself, and herniating or protruding endovascular embolization coils can cause ischemic stroke.

Figure 7B:
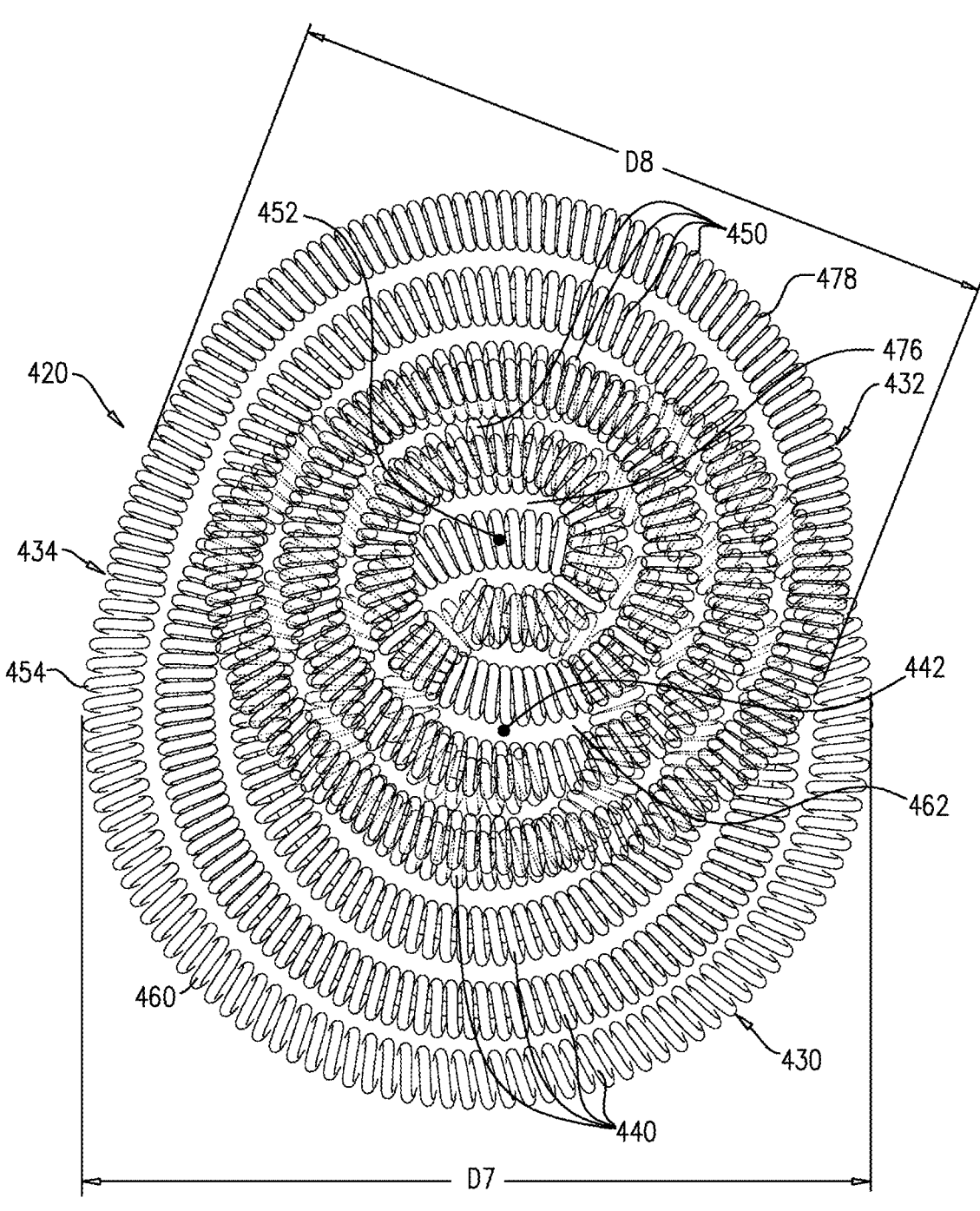

Reference is now made to FIGS. 7A-B, which are schematic illustrations of apparatus 420 for treating a vascular malformation, in accordance with an application of the present invention. Apparatus 420 is configured to bridge the neck of a vascular malformation, such as an aneurysm, e.g., a wide-necked aneurysm, in order to prevent coil herniation, such as described in more detail hereinbelow with reference to FIG. 8. For example, the aneurysm may be of the types described hereinabove with reference to FIGS. 1A-D. Apparatus 420 may implement any of the features of apparatus 20, described hereinabove with reference to FIGS. 1A-2, that are not inconsistent with the features of apparatus 420 described hereinbelow.

Apparatus 420 comprises an orifice section 430, an occlusion section 432, and a connecting section 434. As described in more detail hereinbelow with reference to FIG. 8, orifice section 430 is configured to bridge the neck of the vascular malformation, in order to block blood flow into the aneurysm, thereby embolizing the aneurysm. Upon deployment, occlusion section 432 at least partially occludes an orifice-section central opening 462, as described below.

Apparatus 420 is typically configured such that, when unconstrained (by the patient's anatomy, a microcatheter, or otherwise):

orifice section 430 is shaped so as to define an orifice-section curve 440 that winds at least 2.5 turns (e.g., at least 3 turns), and/or no more than 10 turns, such as between 2.5 (e.g., 3) and 10 turns, around an orifice-section central axis 442 at a changing distance from orifice-section central axis 442 (e.g., at a monotonically changing distance), occlusion section 432 is shaped so as to define an occlusion-section curve 450 that winds at least 2 turns (e.g., at least 2.5 turns), and/or no more than 10 turns, such as between 2 (e.g., 2.5) and 10 turns, around an occlusion-section central axis 452 at a changing distance from occlusion-section central axis 452, connecting section 434 connects orifice-section curve 440 with occlusion-section curve 450 (and optionally has an average radius of curvature that is different from an average radius of curvature of an outermost loop 460 of orifice-section curve 440, orifice-section curve 440 defines orifice-section central opening 462 having an orifice-section-central-opening cross-sectional area equal to at least 2% (e.g., at least 3%, such as at least 5%) of an overall-orifice-section cross-sectional area of orifice-section curve 440 defined by outermost loop 460 of orifice-section curve 440, the orifice-section-central-opening cross-sectional area and the overall-orifice-section cross-sectional area measured perpendicular to orifice-section central axis 442, orifice-section central axis 442 and occlusion-section cen-
tral axis 452 are not coaxial, and a projection of occlusion-section curve 450 occludes at
least 25% (e.g., at least 50%, such as at least 60%) of
the orifice-section-central-opening cross-sectional
area; the projection of occlusion-section curve 450 is in
a direction along orifice-section central axis 442, onto
an orifice-section plane perpendicular to orifice-section
central axis 442.

(In other words, if occlusion-section curve 450 were to be
projected, in a direction along orifice-section central axis
442, onto the orifice-section plane perpendicular to orifice-
section central axis 442, such as shown in FIG. 7B, the
projection of occlusion-section curve 450 would occlude at
least 25% (e.g., at least 50%, such as at least 60%) of the
orifice-section-central-opening cross-sectional area.)

Apparatus 420 typically also has the above-listed charac-
teristics upon implantation in the vascular malformation, in
part because the size of apparatus 420 is selected based on
the size of the vascular malformation.

For some applications, orifice-section curve 440 is a
three-dimensional curve when apparatus 420 is uncon-
strained. For some of these applications, the three-dimen-
sional curve is a conical spiral when apparatus 420 is
unconstrained.

For some applications, apparatus 420 comprises a wire
454 that is shaped so as to define orifice section 430,
occlusion section 432, and connecting section 434. For some
applications, as shown in the figures, wire 454 is micro-
coiled so as to define a primary winding, such as about an
internal wire that may or may not run along the length of
apparatus 420 (labeled for apparatus 20 in FIG. 2). The
curves described herein are macro-curves and do not relate
to this optional micro-coiling, but rather relate to the macro-
structures described herein, such as orifice section 430 and
connecting section 434. For some applications, orifice sec-
tion 430, occlusion section 432, and connecting section 434
comprise one or more shape memory alloys and/or one or
more superelastic alloys.

As labeled in FIG. 7B, orifice-section curve 440 has an
orifice-section outermost diameter D7. Typically, the orifice-
section outermost diameter D7 is at least 2 mm (e.g., at least
4 mm), no more than 10 mm (e.g., no more than 8 mm, such
as no more than 7 mm), and/or between 2 and 10 mm (e.g.,
between 2 and 8 mm, such as between 4 and 7 mm), when
apparatus 420 is unconstrained.

As labeled in FIG. 7B, occlusion-section curve 450 has an
occlusion-section outermost diameter D8. Typically, the
occlusion-section outermost diameter D8 is at least 3 mm
(e.g., at least 4 mm), no more than 10 mm (e.g., no more than
8 mm), and/or between 3 and 10 mm (e.g., between 4 and 8
mm).

For some applications, the occlusion-section outermost
diameter D8 equals between 50% and 150% of the orifice-
section outermost diameter D7 when apparatus 420 is
unconstrained.

For some applications, as shown in the figures, connecting
section 434 connects outermost loop 460 of orifice-section
curve 440 with occlusion-section curve 450 when apparatus
420 is unconstrained. Alternatively, connecting section 434
connects an innermost loop of orifice-section curve 440 with
occlusion-section curve 450 when apparatus 420 is uncon-
strained (configuration not shown).

Connecting section 434 may have any of the properties
(including shapes and dimensions) described hereinabove
with reference to FIGS. 1A-D for connecting section 34.

For some applications, apparatus 420 is configured such
that, when apparatus 420 is unconstrained, the orifice-
section plane is parallel with (as shown) or defines an angle
of less than 30 degrees (e.g., less than 15 degrees) with an
occlusion-section plane perpendicular to occlusion-section
central axis 452. For some applications, apparatus 420 is
configured such that, when apparatus 420 is unconstrained,
the orifice-section plane is parallel with the occlusion-
section plane.

For some applications, such as shown in FIG. 7B, appa-
ratus 420 is configured such that, when apparatus 420 is
unconstrained, occlusion-section central axis 452 does not
pass through orifice-section central opening 462.

For some applications, apparatus 420 is configured such
that, when apparatus 420 is unconstrained, occlusion-section
curve 450 winds a number of turns around occlusion-section
central axis 452, the number of turns equal to at least 0.5
turns (e.g., at least 1 turn) less than a number of turns that
orifice-section curve 440 winds around orifice-section cen-
tral axis 442.

For some applications, apparatus 420 is configured such
that, when apparatus 420 is unconstrained, occlusion-section
curve 450 defines an occlusion-section central opening 476
having an occlusion-section-central-opening cross-sectional
area equal to at least 2% (e.g., at least 3%, such as at least
5%) of an overall-occlusion-section cross-sectional area of
occlusion-section curve 450 defined by an outermost loop
478 of occlusion-section curve 450, the occlusion-section-
central-opening cross-sectional area and the overall-occlu-
sion-section cross-sectional area measured perpendicular to
occlusion-section central axis 452.

For some applications, apparatus 420 is configured such
that, when apparatus 420 is unconstrained, the orifice-
section-central-opening cross-sectional area is at least 0.25
mm2. Alternatively or additionally, for some applications,
apparatus 420 is configured such that, when apparatus 420
is unconstrained, the occlusion-section-central-opening
cross-sectional area is at least 0.25 mm2.

For some applications, as labeled in FIG. 7A, a distance
D9 between a center of mass 464 of orifice-section curve
440 and a center of mass 466 of occlusion-section curve 450,
measured along orifice-section central axis 442, is between
10% (e.g., 20%, such as 25%) and 100% (e.g., 80%, such as
75%), such as between 20% and 80% (e.g., between 25%
and 75%), of the orifice-section outermost diameter D7
(labeled in FIG. 7B) when apparatus 420 is unconstrained.

For some applications, apparatus 420 is configured such
that, when apparatus 420 is unconstrained, a distance
between a geometric center of orifice-section central open-
ing 462 and occlusion-section curve 450, measured along
orifice-section central axis 442, is between 10% (e.g., 20%,
such as 25%) and 100% (e.g., 80%, such as 75%), such as
between 20% and 80% (e.g., between 25% and 75%), of the
orifice-section outermost diameter D7.

For some applications, as labeled in FIG. 1B, an orifice-
section plane 68 perpendicular to orifice-section central axis
42 is parallel with (such as shown in FIG. 1A-D) or defines
an angle of less than 30 degrees with a docking-section plane
70 perpendicular to docking-section central axis 52, when
apparatus 420 is unconstrained. For some of these applica-
tions, orifice-section central axis 42 and docking-section
central axis 52 are coaxial (such as shown in FIG. 1A-D) or
at a distance from each other of less than 50% (e.g., less than
25%) of the orifice-section outermost diameter D7 when
apparatus 420 is unconstrained (configuration not shown).

For some applications, such as shown in FIG. 7A, appa-
ratus 420 is configured such that, when apparatus 420 is unconstrained, orifice-section central axis 442 and occlusion-section central axis 452 are parallel to each other. For some of these applications, orifice-section central axis 442 and occlusion-section central axis 452 are at a distance D10 from each other of between 20% and 80% of the orifice-section outermost diameter D7.

For some applications, a kit is provided that comprises apparatus 420 and a microcatheter in which apparatus 420 is removably disposed for delivery to the vascular malformation. The microcatheter may implement any of the features described hereinabove with reference to FIG. 2 for microcatheter 82.

For some applications, occlusion section 432 is disposed more distally in the microcatheter than is connecting section 434, which in turn is disposed more distally than is orifice section 430.

For some applications, the kit further comprises a pusher tube (such as pusher tube 84, described hereinabove with reference to FIG. 6A), which is removably disposed in the microcatheter with a distal end of the pusher tube removably coupled to a proximal end of orifice section 430.

Figure 8:
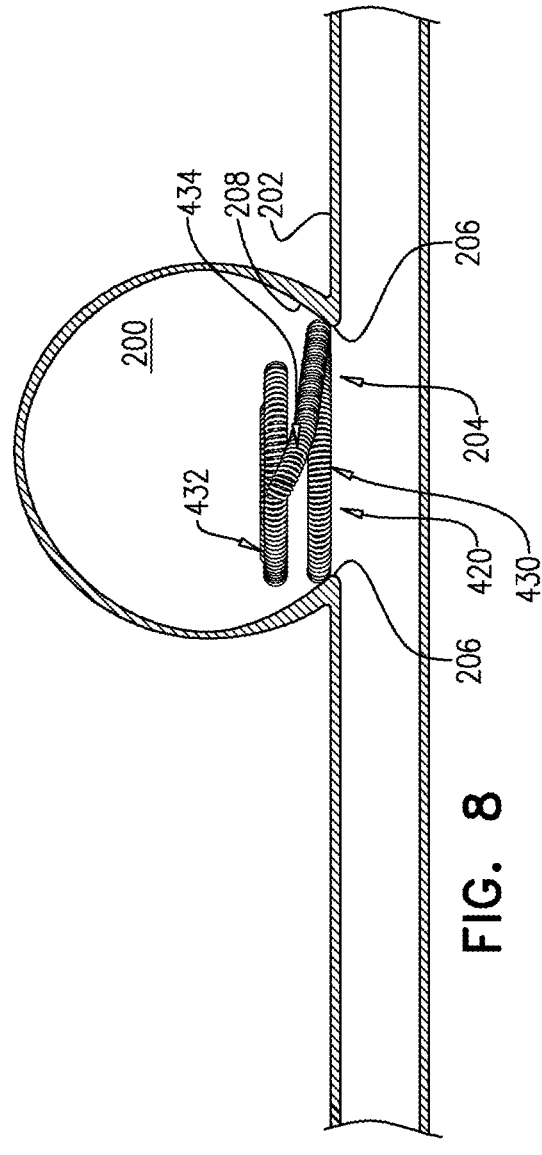
FIG. 8 is a schematic illustration of a deployment of the apparatus of FIGS. 7A-B to treat a vascular malformation, in accordance with an application of the present invention.

Reference is made to FIG. 8, which is a schematic illustration of a deployment of apparatus 420 to treat a vascular malformation, such as aneurysm 200, in accordance with an application of the present invention. Apparatus 420 may be deployed as described hereinabove for apparatus 20 with reference to FIGS. 6A-D.

As shown in FIG. 8, orifice section 430 is deployed from a microcatheter within a portion of the vascular malformation, e.g., aneurysm 200, so as to at least partially cover an orifice 204 of the vascular malformation, the portion of the vascular malformation including one or more anatomical features selected from the group consisting of: a neck 206 of the vascular malformation and a wall 208 of the vascular malformation.

Unlike as described hereinabove with reference to FIG. 6E for apparatus 20, the method of deploying apparatus 420 typically does not comprise implanting endovascular embolization coils 210 in the vascular malformation, e.g., aneurysm 200. Instead, orifice section 430 is configured to bridge the neck of the vascular malformation, in order to block blood flow into the aneurysm, thereby embolizing the aneurysm. Upon deployment, occlusion section 432 at least partially occludes orifice-section central opening 462, thereby reducing blood flow through orifice-section central opening 462 and obviating the need to also implant endovascular embolization coils 210 in the vascular malformation. Even though occlusion section 432 typically does not touch orifice section 430 around the perimeter of orifice-section central opening 462 and there is a gap between occlusion section 432 and orifice-section central opening 462, this gap is small enough to reduce blood flow sufficiently to effectively occlude orifice-section central opening 462 over a relatively short period of time.

Alternatively, endovascular embolization coils 210 are additionally implanted, such as described hereinabove with reference to FIG. 6E for apparatus 20.

In an embodiment, techniques and apparatus described in one or more of the following applications, which are incorporated herein by reference, are combined with techniques and apparatus described herein:

US Patent Application Publication 2017/0367708 to Mayer et al.

PCT Publication WO 2017/221252 to Mayer et al.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. Apparatus for treating a vascular malformation, the apparatus comprising:
   an orifice section having two endpoints;
   an intra-vascular-malformation docking section; and
   a connecting section having two endpoints,
   wherein the apparatus is configured such that, when unconstrained:
      the orifice section is shaped so as to define a spiral orifice-section curve that winds at least 2.5 turns around an orifice-section central axis at a changing distance from the orifice-section central axis,
      the intra-vascular-malformation docking section is shaped so as to define a docking-section curve that winds between 0.5 and 2 turns around a docking-section central axis at a changing or constant distance from the docking-section central axis,
      a connecting-section slope of the connecting section equals the quotient of (a) a rise distance between the two endpoints of the connecting section, measured along the orifice-section central axis, divided by (b) a run distance equal to a length of the connecting section between the two endpoints of the connecting section, measured along the connecting section,
      an orifice-section slope of the orifice section equals the quotient of (a) a rise distance between the two endpoints of the orifice section, measured along the orifice-section central axis, divided by (b) a run distance equal to a length of the orifice section between the two endpoints of the orifice section, measured along the orifice section, and
      the connecting-section slope is greater than the orifice-section slope.

2. The apparatus according to claim 1, wherein the apparatus is configured such that, when the apparatus is unconstrained:
   the connecting-section slope is greater than 10%.

3. The apparatus according to claim 1, wherein the apparatus is configured such that, when the apparatus is unconstrained, the connecting section connects the outermost loop of the orifice-section curve with the docking-section curve.

4. The apparatus according to claim 1, wherein the apparatus is configured such that, when the apparatus is unconstrained, the docking-section curve has between 0.75 and 2 turns.

5. The apparatus according to claim 4, wherein the apparatus is configured such that, when the apparatus is unconstrained, the docking-section curve has between 1 and 2 turns.

6. The apparatus according to claim 1, wherein the apparatus is configured such that, when the apparatus is unconstrained, the docking-section curve has between 0.5 and 1.25 turns.

7. The apparatus according to claim 6, wherein the apparatus is configured such that, when the apparatus is unconstrained, the docking-section curve has between 0.75 and 1.25 turns.

8. The apparatus according to claim 7, wherein the apparatus is configured such that, when the apparatus is unconstrained, the docking-section curve has between 0.9 and 1.1 turns.

9. The apparatus according to claim 1, wherein the apparatus is configured such that, when the apparatus is unconstrained, the connecting section is straight.

10. The apparatus according to claim 1, wherein the apparatus is configured such that, when the apparatus is unconstrained, a closest distance between the orifice-section curve and the docking-section curve, measured along the orifice-section central axis, is between 4% and 50% of an orifice-section outermost diameter of the orifice-section curve.

11. The apparatus according to claim 1, wherein the apparatus is configured such that, when the apparatus is unconstrained, a distance between a center of mass of the orifice-section curve and a center of mass of the docking-section curve, measured along the orifice-section central axis, is between 10% and 50% of an orifice-section outermost diameter of the orifice-section curve.

12. The apparatus according to claim 1, wherein the apparatus is configured such that, when the apparatus is unconstrained, an orifice-section plane perpendicular to the orifice-section central axis is parallel with or defines an angle of less than 30 degrees with a docking-section plane perpendicular to the docking-section central axis.

13. The apparatus according to claim 1, wherein the apparatus is configured such that, when the apparatus is unconstrained, an orifice-section plane perpendicular to the orifice-section central axis defines an angle of greater than 60 degrees with a docking-section plane perpendicular to the docking-section central axis.

14. The apparatus according to claim 1, wherein the apparatus comprises a wire that is shaped so as to define the orifice section, the intra-vascular-malformation docking section, and the connecting section, when the apparatus is unconstrained.

15. The apparatus according to claim 1, wherein the apparatus is configured such that, when the apparatus is unconstrained, the spiral orifice-section curve is a conical spiral.

16. The apparatus according to claim 1, wherein the apparatus is configured such that, when the apparatus is unconstrained, the docking-section curve winds around the docking-section central axis at the constant distance from the docking-section central axis.

17. A kit comprising the apparatus according to claim 1, the kit further comprising a microcatheter in which the apparatus is removably disposed for delivery to the vascular malformation.

18. The kit according to claim 17, wherein the intra-vascular-malformation docking section is disposed more distally in the microcatheter than is the connecting section, which in turn is disposed more distally than is the orifice section.

19. The kit according to claim 17, wherein the kit further comprises a pusher tube, which is removably disposed in the microcatheter with a distal end of the pusher tube removably coupled to a proximal end of the orifice section.

20. A method for treating a vascular malformation, the method comprising:

providing an apparatus including an orifice section having two endpoints, an intra-vascular-malformation docking section, and a connecting section having two endpoints, the apparatus configured such that, when unconstrained:

the orifice section is shaped so as to define a spiral orifice-section curve that winds at least 2.5 turns around an orifice-section central axis at a changing distance from the orifice-section central axis, the intra-vascular-malformation docking section is shaped so as to define a docking-section curve that winds between 0.5 and 2 turns around a docking-section central axis at a changing or constant distance from the docking-section central axis, a connecting-section slope of the connecting section equals the quotient of (a) a rise distance between the two endpoints of the connecting section, measured along the orifice-section central axis, divided by (b) a run distance equal to a length of the connecting section between the two endpoints of the connecting section, measured along the connecting section, an orifice-section slope of the orifice section equals the quotient of (a) a rise distance between the two endpoints of the orifice section, measured along the orifice-section central axis, divided by (b) a run distance equal to a length of the orifice section between the two endpoints of the orifice section, measured along the orifice section, and the connecting-section slope is greater than the orifice-section slope;

implanting (a) the intra-vascular-malformation docking section within the vascular malformation, (b) a connecting section of the apparatus, and (c) the orifice section within a portion of the vascular malformation so as to at least partially cover an orifice of the vascular malformation, the portion of the vascular malformation including one or more anatomical features selected from the group consisting of: a neck of the vascular malformation and a wall of the vascular malformation; and implanting endovascular embolization coils in the vascular malformation such that the endovascular embolization coils become entangled with the intra-vascular-malformation docking section.

21. The method according to claim 20, wherein providing the apparatus comprises providing the apparatus configured such that, when the apparatus is unconstrained, the spiral orifice-section curve is a conical spiral.

22. The method according to claim 20, wherein implanting the intra-vascular-malformation docking section, the connecting section, and the orifice section comprises:

inserting the intra-vascular-malformation docking section, the connecting section, and the orifice section into a blood vessel while removably disposed in a microcatheter;

deploying the intra-vascular-malformation docking section from the microcatheter into the vascular malformation;

thereafter, deploying the connecting section from the microcatheter; and thereafter, deploying the orifice section from the microcatheter within the portion of the vascular malformation.

* * * * *